United States Patent
Ma et al.

(10) Patent No.: US 11,986,525 B2
(45) Date of Patent: May 21, 2024

(54) LOW-DOSE RADIATION THERAPY FOR TRAUMATIC BRAIN INJURY AND STROKE

(71) Applicant: City University of Hong Kong, Hong Kong (CN)

(72) Inventors: Chi Him Eddie Ma, Hong Kong (CN); Ngan Pan Bennett Au, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 374 days.

(21) Appl. No.: 17/449,959

(22) Filed: Oct. 5, 2021

(65) Prior Publication Data
US 2022/0111229 A1   Apr. 14, 2022

Related U.S. Application Data

(60) Provisional application No. 63/089,607, filed on Oct. 9, 2020.

(51) Int. Cl.
| | |
|---|---|
| A61K 45/06 | (2006.01) |
| A61K 39/00 | (2006.01) |
| A61N 5/10 | (2006.01) |
| A61P 25/00 | (2006.01) |
| C07K 16/28 | (2006.01) |

(52) U.S. Cl.
CPC .............. *A61K 45/06* (2013.01); *A61N 5/10* (2013.01); *A61P 25/00* (2018.01); *C07K 16/2845* (2013.01); *A61K 2039/505* (2013.01); *A61N 2005/1091* (2013.01)

(58) Field of Classification Search
None
See application file for complete search history.

(56) References Cited

U.S. PATENT DOCUMENTS

| | | | |
|---|---|---|---|
| 5,511,563 A | 4/1996 | Diamond | |
| 5,692,509 A | 12/1997 | Voss et al. | |
| 2013/0323166 A1* | 12/2013 | Fontanesi | A61N 5/1001 424/1.49 |
| 2016/0367837 A1* | 12/2016 | Moore | A61B 5/4088 |

FOREIGN PATENT DOCUMENTS

RU    2018100668 A    7/2019

OTHER PUBLICATIONS

Morries et al. "Treatments for traumatic brain injury with emphasis on transcranial near-infrared laser phototherapy" Neuropsychiatric Disease and Treatment 11, 2159-2175 (2015). (Year: 2015).*
Oron et al. "Low-Level Laser Therapy Applied Transcranially to Mice following Traumatic Brain Injury Significantly Reduces Long-Term Neurological Deficit" Journal of Neurotrauma vol. 24 No. 4 651-656 (2007) (Year: 2007).*
Jang et al. "Radiation Therapy for Heterotopic Ossification in a patient with Traumatic Brain Injury" Yonsei Medical Journal, vol. 41 No. 4, 536-539 (2000) (Year: 2000).*

* cited by examiner

*Primary Examiner* — Edwin C Gunberg
(74) *Attorney, Agent, or Firm* — S&F/WEHRW

(57) ABSTRACT

Provided herein is a method of treating a traumatic brain injury in a subject in need thereof, the method including administering to the subject a therapeutically effective amount of radiation. The methods can improve motor function recovery and reverse motor function deficits after traumatic brain injury and/or ischemic stroke in a subject.

Figure 1:
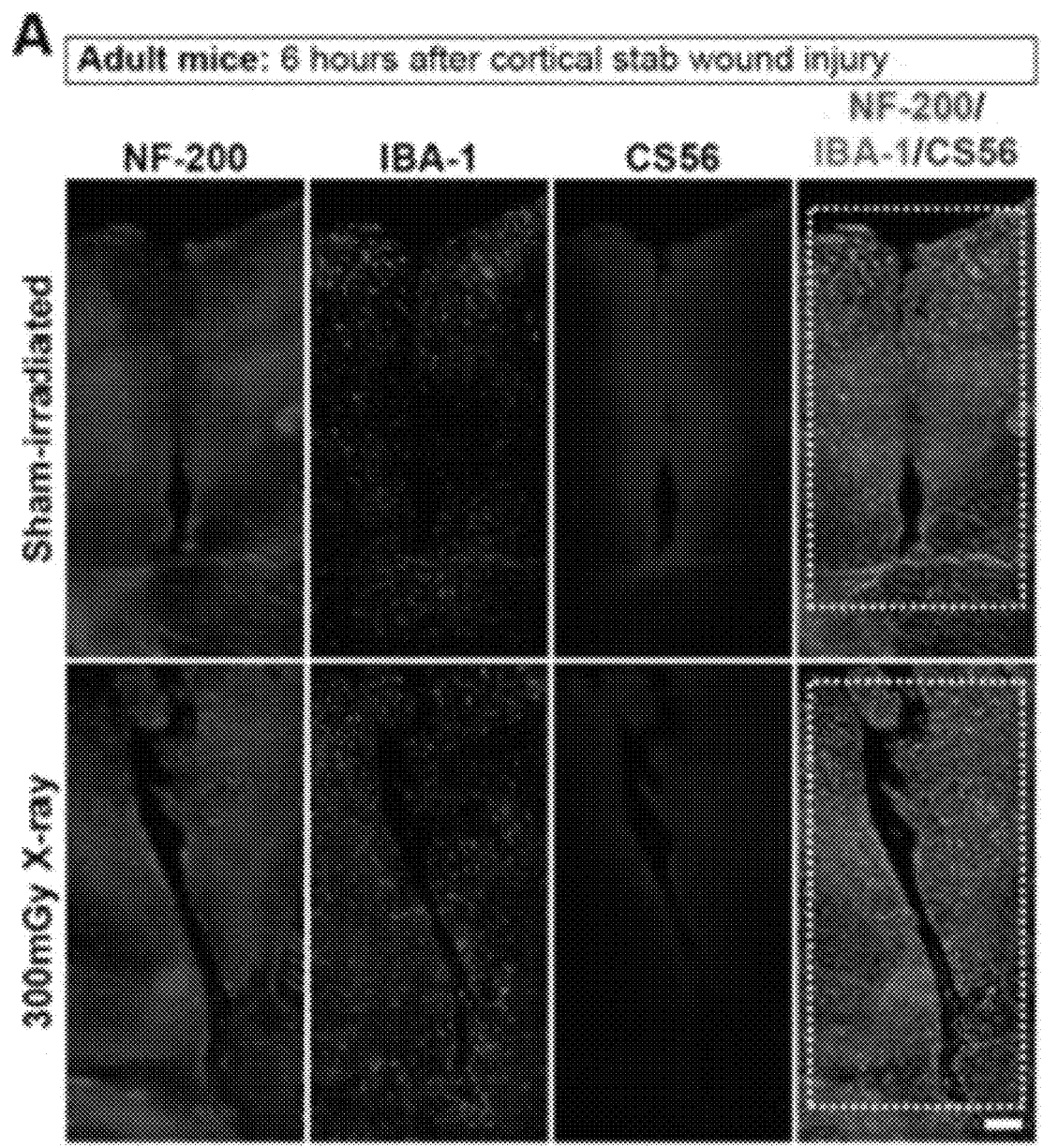
Figure 1:
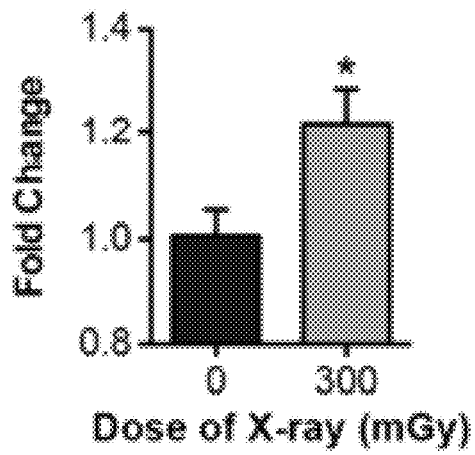
Figure 1:
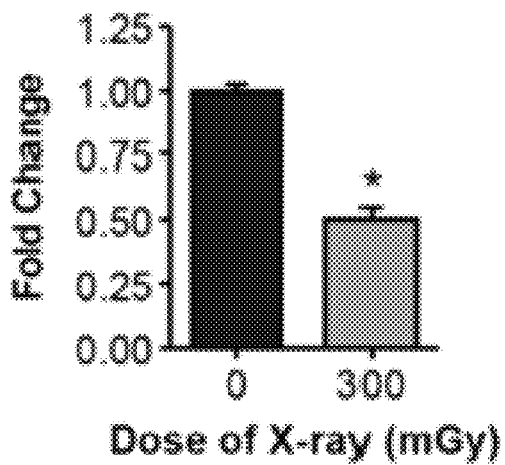

19 Claims, 20 Drawing Sheets
(17 of 20 Drawing Sheet(s) Filed in Color)

LOW-DOSE RADIATION THERAPY FOR TRAUMATIC BRAIN INJURY AND STROKE

CROSS-REFERENCE TO RELATED APPLICATIONS

This application claims priority from U.S. Provisional Patent Application No. 63/089,607 filed on Oct. 9, 2020, the content of which is hereby incorporated by reference in its entirety.

TECHNICAL FIELD

The present disclosure relates to a method of treating neurological disorders, such as traumatic brain injury and stroke, in a subject in need thereof comprising the use of low dose radiation.

BACKGROUND

Brain diseases or injuries, such as traumatic brain injury (TBI) and stroke, are common in today's world. Significant amount of resources are used on treatment, hospitalization, and rehabilitation of patients with brain diseases. Among other diseases, TBI remains one of the leading causes of mortality and morbidity at all age groups in all countries. Currently, more than 50 million people suffer from TBI of different severities every year. Patients with moderate or severe TBI may suffer from permanent and irreversible motor functions, and as a result, may have lost their ability to work and even self-care after the incidence of TBI. This creates a high financial burden to the patients, their families and the community. To date, there has been no known effective treatment for TBI, e.g., to restore the motor functions. On the other hand, survivors of TBI and ischemic stroke may have irreversible sensory, motor, and/or cognitive function deficits. There is a need for treating these survivors to improve or otherwise alleviate their conditions.

SUMMARY

This disclosure explores, generally, the therapeutic potential of low dose (LD) X-ray in a subject (e.g., humans). The examples below concern, more particularly, the therapeutic potential of whole-body LD or brain X-ray irradiation in promoting motor functional recovery after TBI and stroke in a subject.

In one experiment performed using mice, immediately after TBI or stroke induction, the mice received an acute single exposure to LD X-ray irradiation. After TBI, in LD X-ray irradiated mice, at 6 hours and 7 days post-injury, there is a marked increase in microglia density, and reduced deposition of a growth inhibitory extracellular matrix chondroitin sulfate proteoglycans. In LD X-ray irradiated mice, the wound area was also significantly reduced 7 days after injury. Similar beneficial effects were observed in LD X-ray irradiated mice after stroke. Significantly, LD X-ray irradiated mice showed marked improvement in motor function as demonstrated by narrow beam walking, pole climbing, and grip strength tests after TBI and stroke, while sham-irradiated mice showed irreversible motor functional deficits after stroke. LD X-ray irradiation restored brain activity measured by electroencephalogram, induced axonal sprouting, and facilitated brain rewiring after stroke. This suggests a strong therapeutic potential of LD X-ray irradiation in treating TBI and stoke.

The data presented herein demonstrates that LD X-ray irradiation, such as whole-body LD X-ray irradiation, can advantageously accelerate motor function recovery after TBI and reverse motor function deficits after ischemic stroke.

In a first aspect, provided herein is a method of treating a traumatic brain injury in a subject in need thereof, the method comprising administering to the subject a therapeutically effective amount of radiation.

In certain embodiments, the radiation is selected from the group consisting of X-ray radiation, gamma ray radiation, and a combination thereof.

In certain embodiments, 10,000 mGy or less of radiation is administered to the subject.

In certain embodiments, about 2,000 mGy to about 6,000 mGy of radiation is administered to the subject.

In certain embodiments, the radiation is administered to the subject at a rate of 200 mGy/min or less.

In certain embodiments, the radiation is administered to the subject at a rate of about 50 to about 150 mGy/min.

In certain embodiments, the radiation is administered to the brain.

In certain embodiments, the radiation is administered to the whole-body.

In certain embodiments, the traumatic brain injury comprises a mild traumatic brain injury, a moderate traumatic brain injury, or a severe traumatic brain injury.

In certain embodiments, the traumatic brain injury comprises a moderate traumatic brain injury or a severe traumatic brain injury.

In certain embodiments, the traumatic brain injury comprises a stroke.

In certain embodiments, the stroke is an ischemic stroke, a hemorrhagic stroke, a transient ischemic attack, or a brain stem stroke.

In certain embodiments, the traumatic brain injury comprises an ischemic stroke.

In certain embodiments, the method further comprises the step of co-administering a therapeutically effective amount of a traumatic brain injury therapeutic.

In certain embodiments, the traumatic brain injury therapeutic is selected from the group consisting of a neuroprotective agent, a thrombolytic agent, a glycoprotein IIb/IIIa receptor antagonist, and an anti-CD 18 antibody.

In certain embodiments, the method comprises administering to the brain or the whole-body of the subject about 10,000 mGy or less of X-ray radiation, gamma ray radiation, or a combination thereof.

In certain embodiments, the method comprises administering to the brain or the whole-body of the subject about 200 mGy to about 400 mGy of X-ray radiation.

In certain embodiments, the radiation is administered to the brain and the traumatic brain injury comprises a stroke.

In certain embodiments, the method comprises administering to the brain of the subject about 200 mGy to about 400 mGy of X-ray radiation and the traumatic brain injury comprises an ischemic stroke.

In certain embodiments, the method comprises administering to the brain of the subject X-ray radiation at a rate of about 75 mGy/min to about 100 mGy/min and the traumatic brain injury comprises an ischemic stroke.

BRIEF DESCRIPTION OF TH DRAWINGS

The patent or application file contains at least one drawing executed in color. Copies of this patent or patent application publication with color drawing(s) will be provided by the Office upon request and payment of the necessary fee.

The above and other objects and features of the present disclosure will become apparent from the following description of the disclosure, when taken in conjunction with the accompanying drawings.

FIG. 1 depicts low dose (LD) X-ray irradiation promotes microglia migration towards the injury site 6 hours after stab wound injury on adult cortices. (A) More IBA-1-positive microglia were colonized on the injury site (white dotted line) in X-ray irradiated mice 6 hours after injury, compared with their respective sham-irradiated controls. Scale bar: 200 μm. (B) The microglial density in the injured hemisphere of X-ray irradiated mice were significantly higher than that of sham-irradiated mice. (C) Less CSPG (as assessed by the immunoreactivity of anti-CS-56) was deposited at the injury site in X-ray irradiated mice. Mean±SEM (n=3 per group). *P<0.05. Student's t-test in (B-C).

Figure 2:
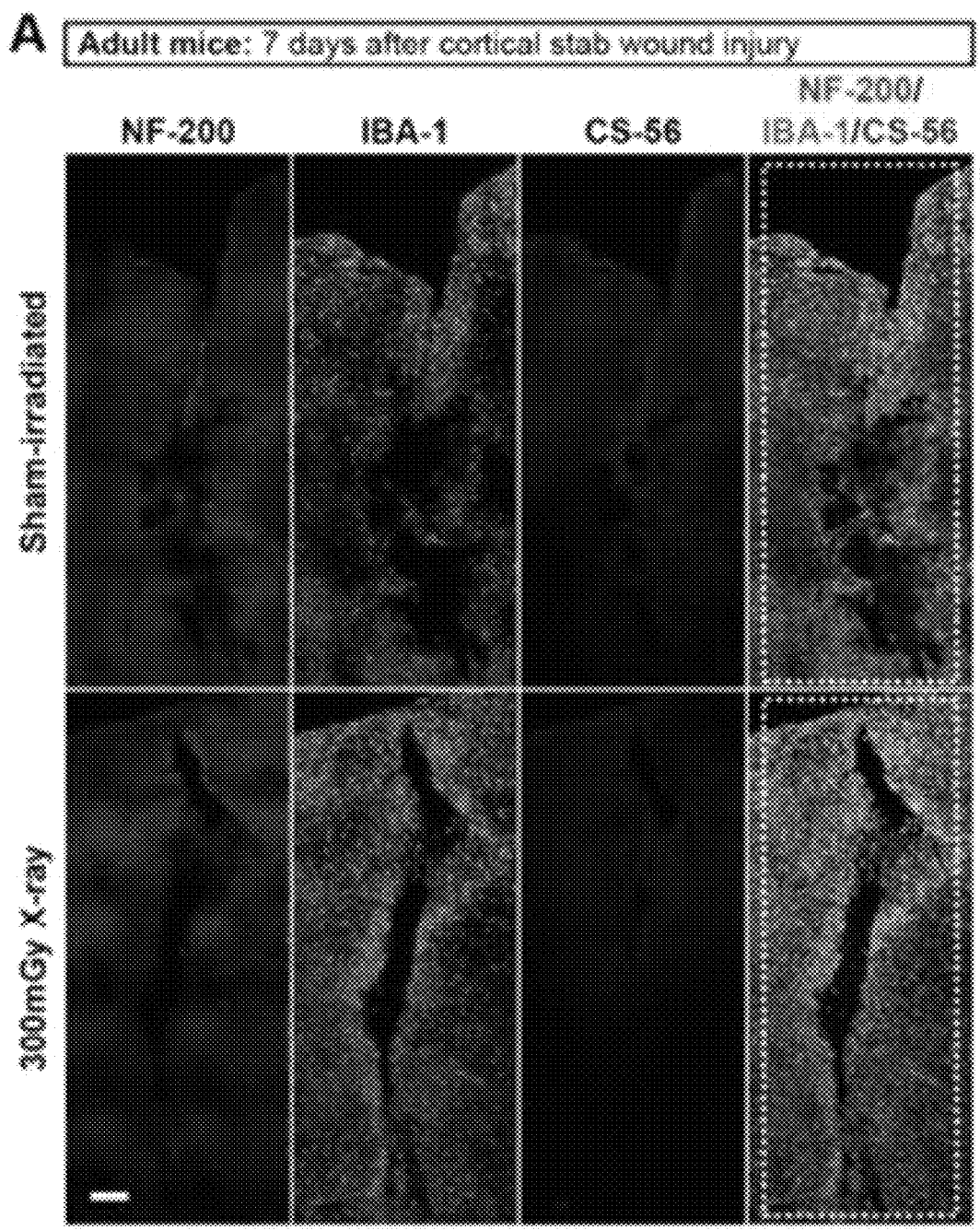
Figure 2:
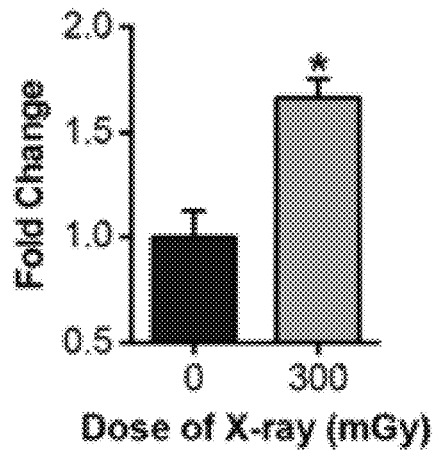
Figure 2:
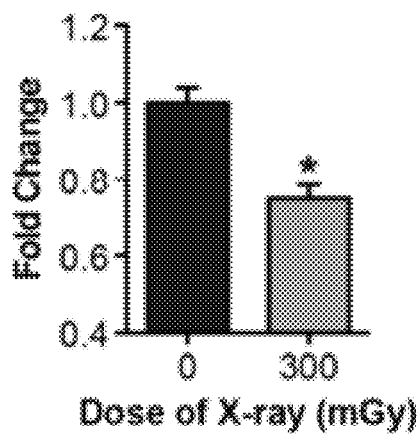

FIG. 2 depicts LD X-ray irradiation reduces CSPG deposition at the injury site 7 days after stab wound injury on adult cortices. (A) Fluorescent micrographs revealed an increased number of IBA-1-positive microglia colonized at the injury site (white dotted line) in X-ray irradiated mice 7 days after injury. Scale bar: 200 μm. (B) The microglial density in the injured hemisphere of X-ray irradiated mice. LD X-ray were significantly higher than that of sham-irradiated mice. (C) Less CSPG (as assessed by the immunoreactivity of anti-CS-56) was deposited at the injury site in X-ray irradiated mice. Mean±SEM (n=3 per group). *P<0.05. Student's t-test in (B-C).

Figure 3:
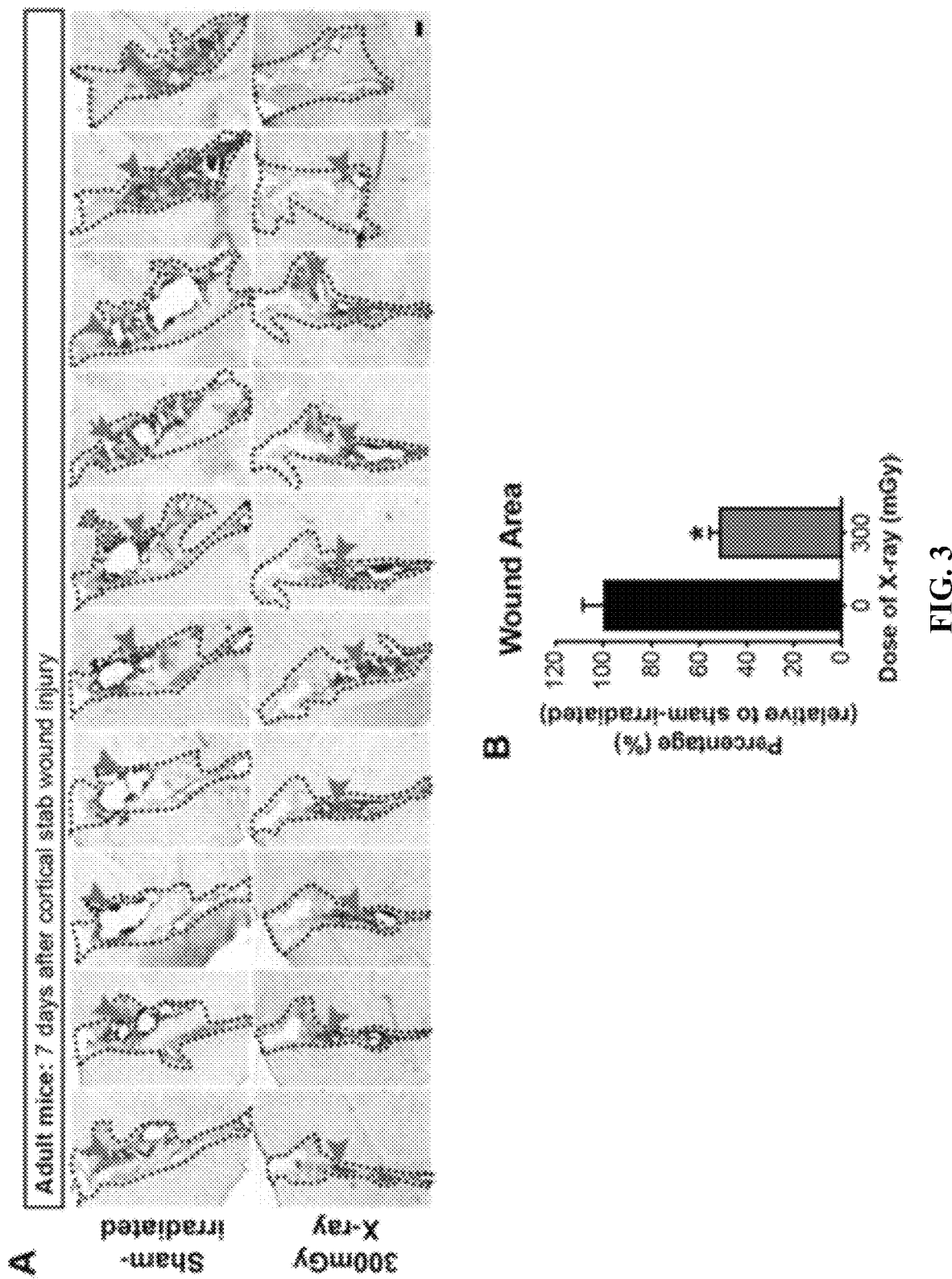

FIG. 3 depicts LD X-ray irradiation accelerates wound closure 7 days after TBI in adult mice. (A) Serial sagittal sections of adult cortices from both sham- and LD X-ray irradiated mice were stained with cresyl violet. The dotted area indicated the site of injury. Intracerebral hemorrhage yielded dark brownish color indicated by green arrowheads. Scale bar: 200 μm. (B) LD X-ray irradiation accelerated wound closure as reflected by smaller wound area than sham-irradiated mice. Mean±SEM (n=3 per group). *P<0.05. Student's t-test.

Figure 4:
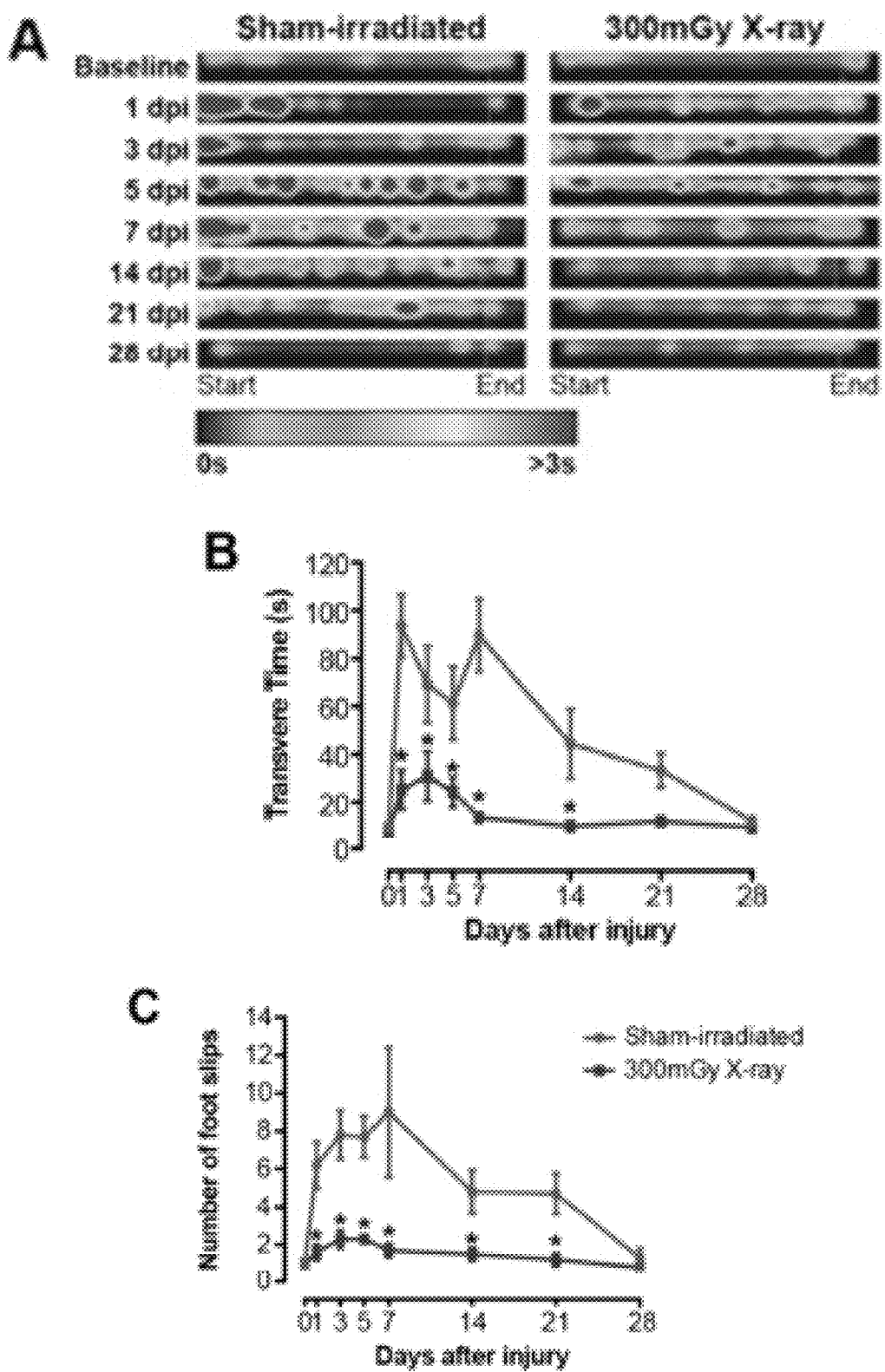
Figure 4:
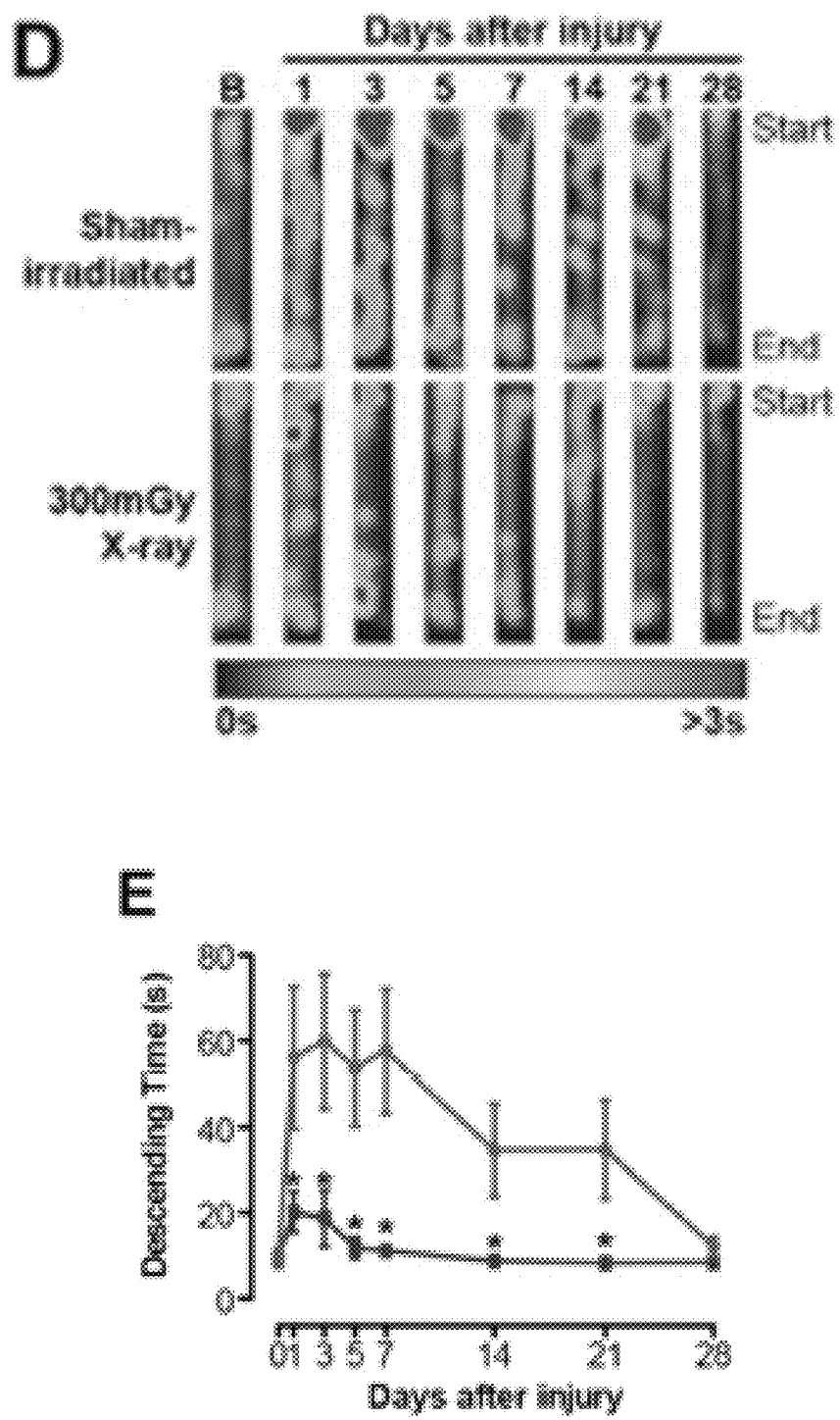
Figure 4:
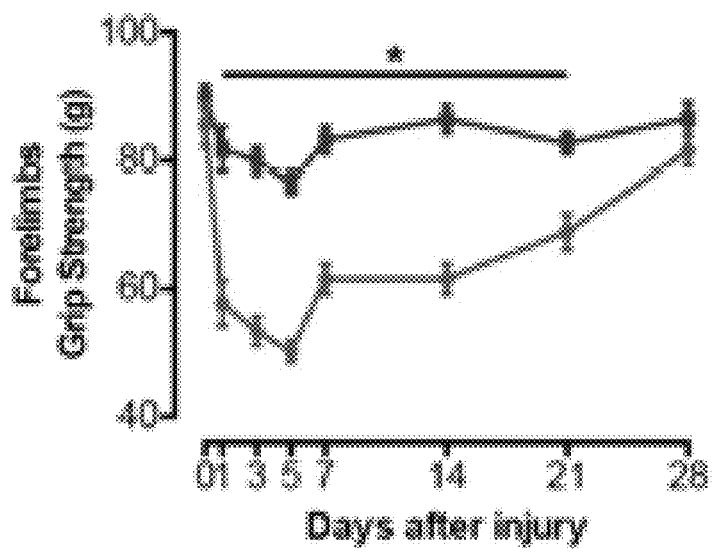
Figure 4:
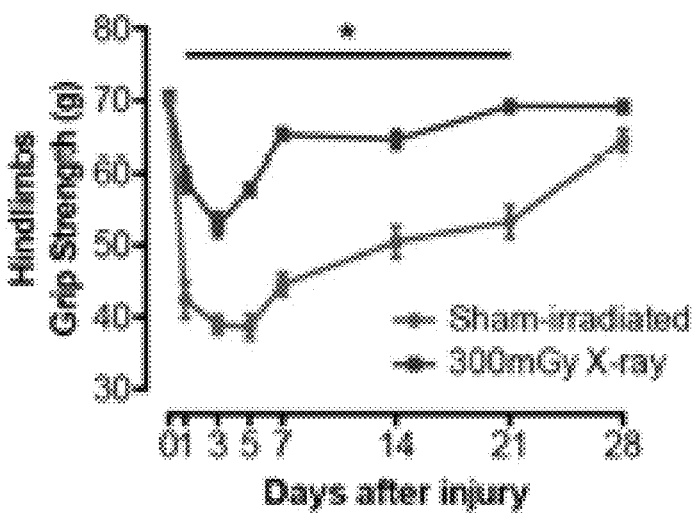

FIG. 4 depicts LD X-ray irradiation reverses motor function deficit after TBI in mice. The mice were received a single whole-body LD X-ray irradiation at 300 mGy immediately after cortical stab wound injury on motor cortices of adult male C57BL/6 mice. Motor functional recovery was assessed by narrow beam walking, pole climbing, and grip strength tests for a period of 28 days. (A) In narrow beam walking, heat-map plots of the mouse position generated by ANY-maze automated video tracking system (Stoelting, USA) revealed that sham-irradiated TBI mice tended to remain immobile at the starting-point during the first three days after TBI. Strikingly, LD X-ray irradiated mice successfully crossed the beam immediately after TBI at 1 dpi. (B) Sham-irradiated mice took much longer time than LD X-ray irradiated mice to transverse the beam at all time points due to the fact that they made frequent stops for resting and stabilizing on the beam. (C) LD X-ray irradiated mice made significantly fewer foot slip errors than sham-irradiated mice. (D) In pole climbing, heat-map plots showed that sham-irradiated mice spent most of the time at the top of the pole and only managed to descend the pole properly till 28 dpi. (E) Notably, the time taken to descend the pole in X-ray irradiated mice was significantly lower than the sham-irradiated mice at all time points after TBI. (F and G). The grip strength of forelimbs or hindlimbs were measured using grip strength meter (GT-3, Bioseb). LD X-ray irradiated mice demonstrated a faster recovery on grip strength of forelimbs (F) and hindlimbs (G) than the sham-irradiated mice. Mean±SEM (n=10 per group). *P<0.05; twoway ANOVA with repeated measures, followed by Bonferroni's post hoc test.

Figure 5:
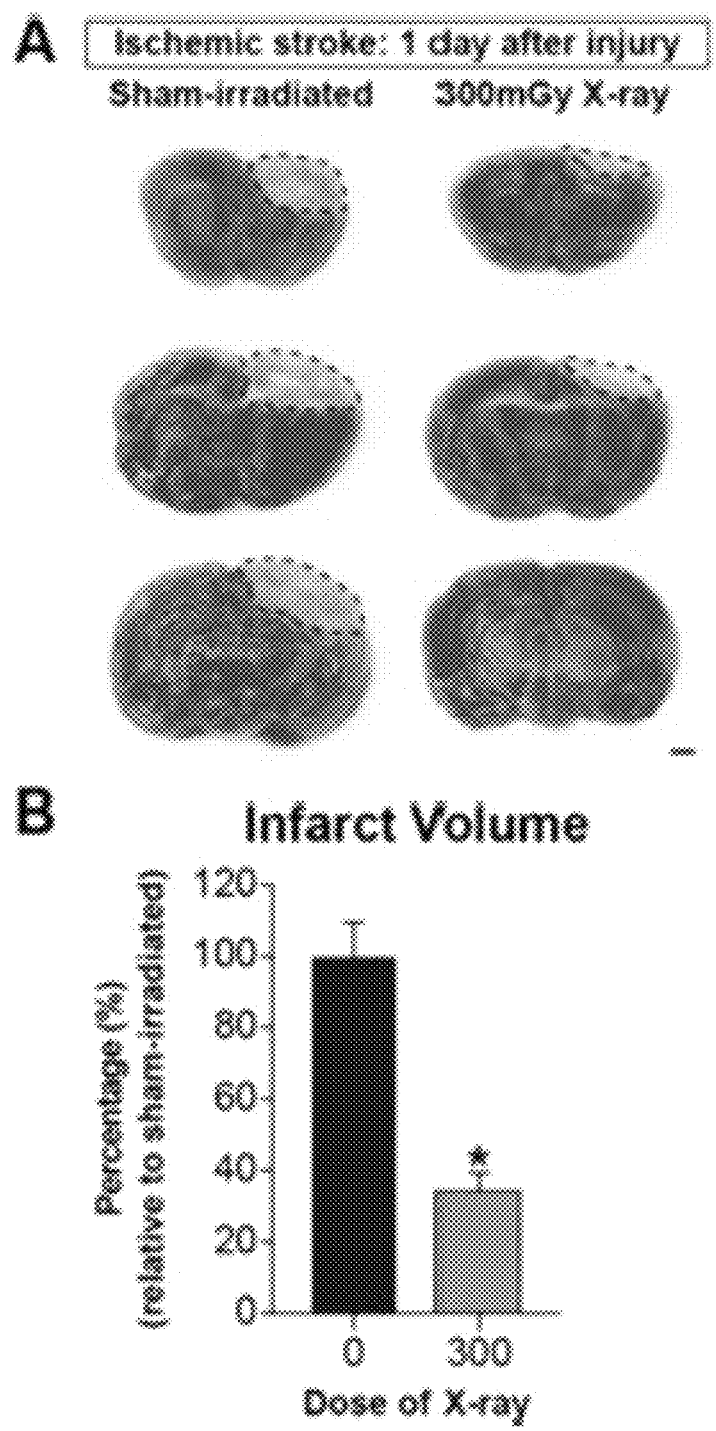
Figure 5:
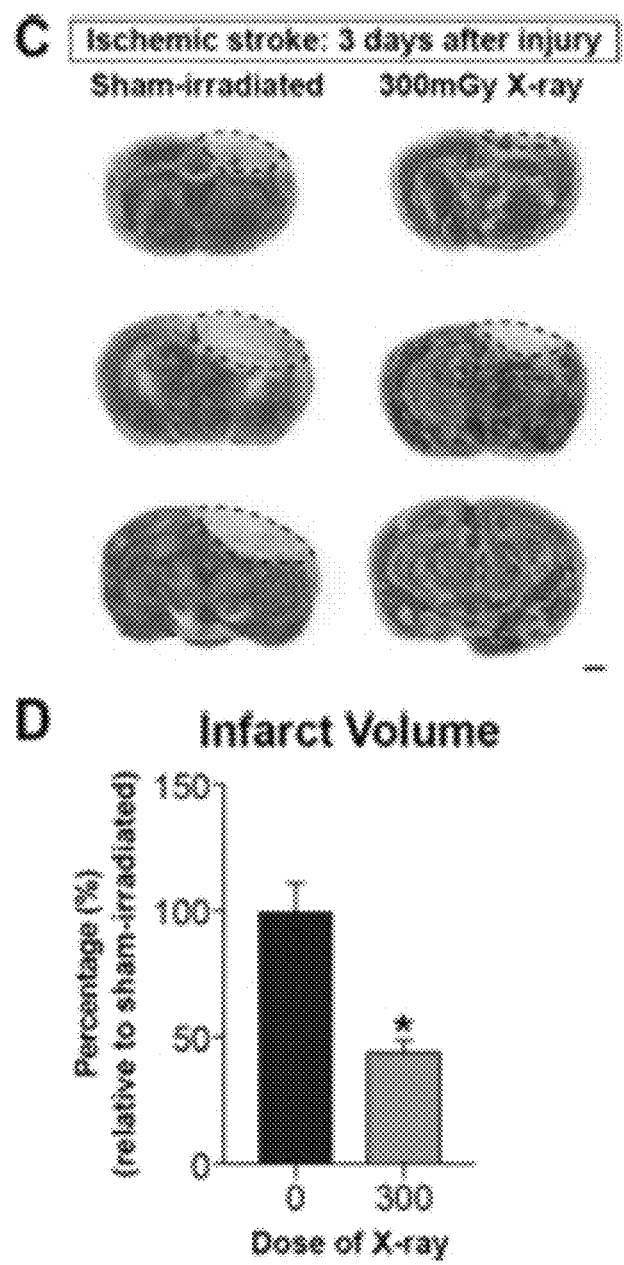

FIG. 5 depicts LD X-ray irradiation reduces the brain infract volume after ischemic stroke. Immediately after stroke induction, the mice were received a single exposure of whole-body LD X-ray irradiation at 300 mGy. At day 1 and day 3 post stroke, the brain was freshly dissected and cut into 2-mm-thick brain slices. The brain slices were then stained with 2% TTC solution for infract volume measurement. (A and B) Photothrombotic stroke induced a substantial damage to the motor cortex (black inset in A) in the sham-irradiated mice at day 1 after ischemic stroke. In contrast, the infract volume was markedly reduced in LD X-ray irradiated mice. (C and D) While sham-irradiated mice still exhibited a large infract in the motor cortex 3 days after stroke, a large volume of brain remained intact after stroke induction in LD X-ray irradiated mice, further demonstrating its neuroprotective effects. Scale: 500 μm in (A and C). Mean±SEM (n=6-8 per group) *P<0.05, Student's t-test.

Figure 6:
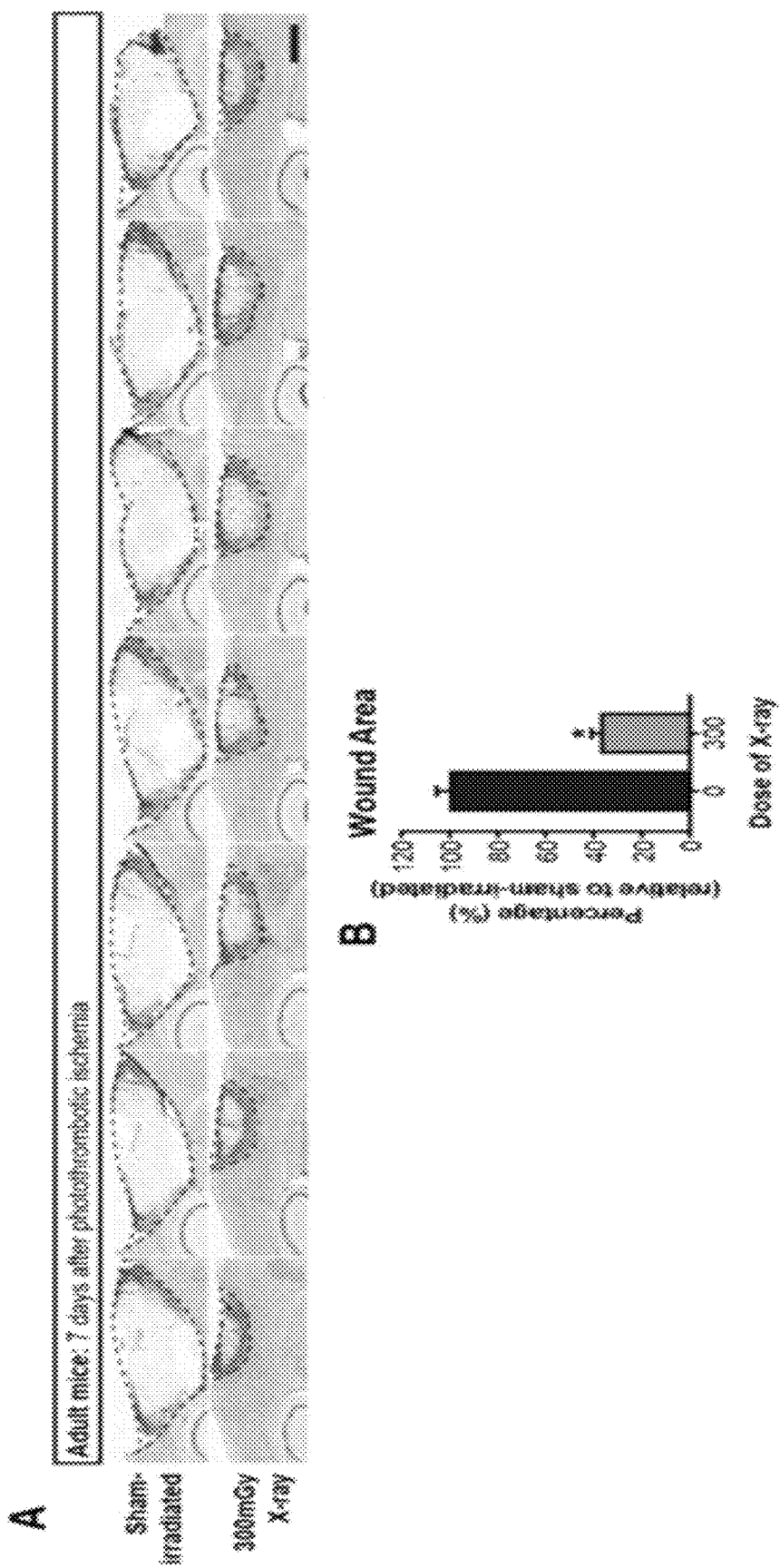

FIG. 6 depicts LD X-ray irradiation promotes wound closure 7 days after ischemic stroke. (A) Serial sagittal sections of adult cortices from both sham- and LD X-ray irradiated mice were stained with cresyl violet. The dotted area indicated the infract area after stroke induction. Scale bar: 1,000 μm. (B) Quantification of wound area revealed that LD X-ray irradiation speed up the wound closure after ischemic stroke. Mean±SEM (n=3 per group). *P<0.05. Student's t-test.

Figure 7:
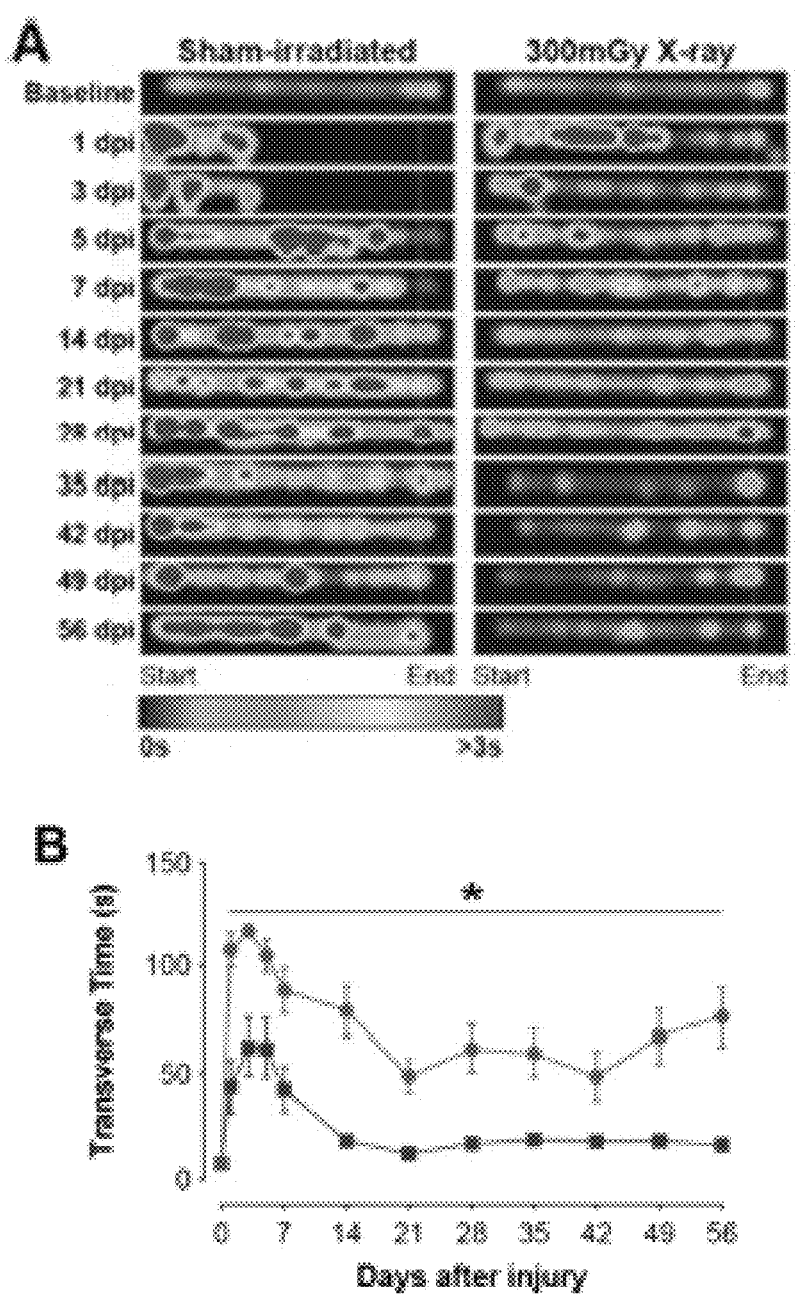
Figure 7:
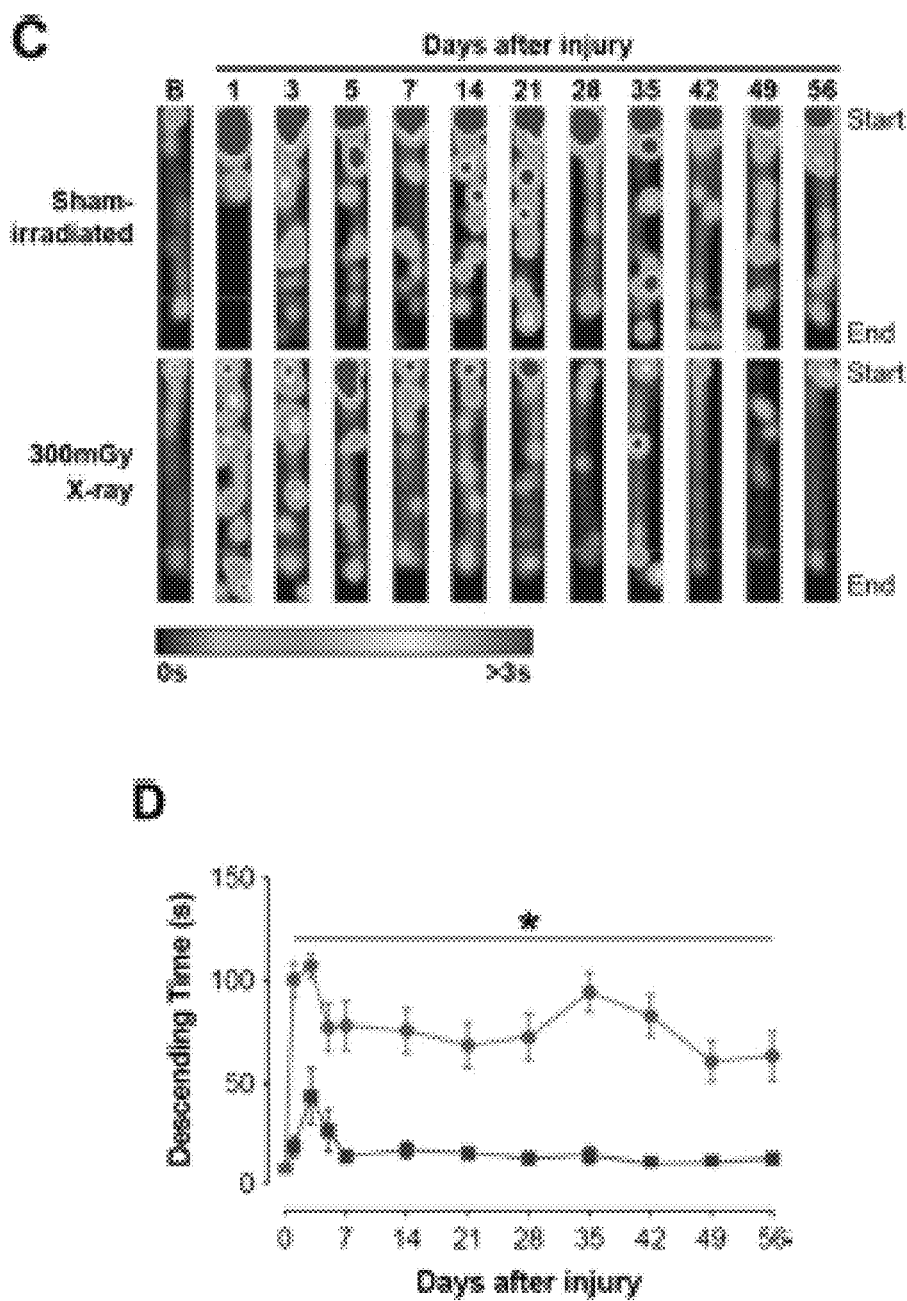
Figure 7:
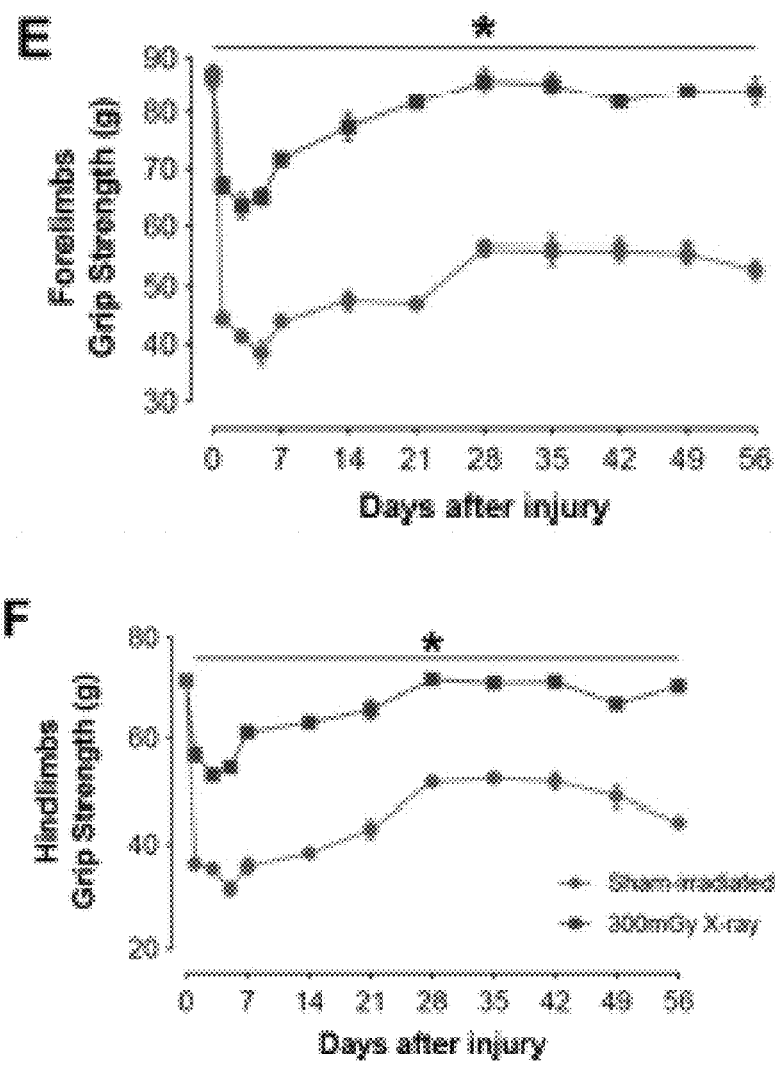

FIG. 7 depicts LD X-ray irradiation restores motor function deficit after ischemic stroke in mice. The mice were received a single whole-body LD X-ray irradiation at 300 mGy immediately after ischemic stroke induced by photothrombosis on motor cortices of adult male C57BL/6 mice. Motor functional recovery was assessed by narrow beam walking, pole climbing, and grip strength tests for a period of 56 days. (A) Sham-irradiated mice intended to remain immobile at the starting point during the first three days after ischemic stroke, and made frequent stops to rest and stabilize themselves before reaching the destination in the subsequent days. In contrast, LD X-ray irradiated mice successfully transversed the beam even 1 day after ischemic stroke. (B) Sham-irradiated mice took significantly longer time to transverse the narrow beam compared with LD X-ray irradiated mice. (C) Sham-irradiated mice spent significant amount of time at the top of the pole during the entire course of experiments and failed to descend the pole properly. (D) LD X-ray irradiated mice took significantly less time to descend the pole compared with sham-irradiated controls. (E and F) The grip strength of forelimbs (E) and hindlimbs (F) in LD X-ray irradiated mice remained significantly larger than sham-irradiated mice, demonstrating a faster recovery on grip strength in LD X-ray irradiated mice after ischemic stroke. Mean±SEM (n=12-13 per group). *P<0.05; two-way ANOVA with repeated measures, followed by Bonferroni's post hoc test.

Figure 8:
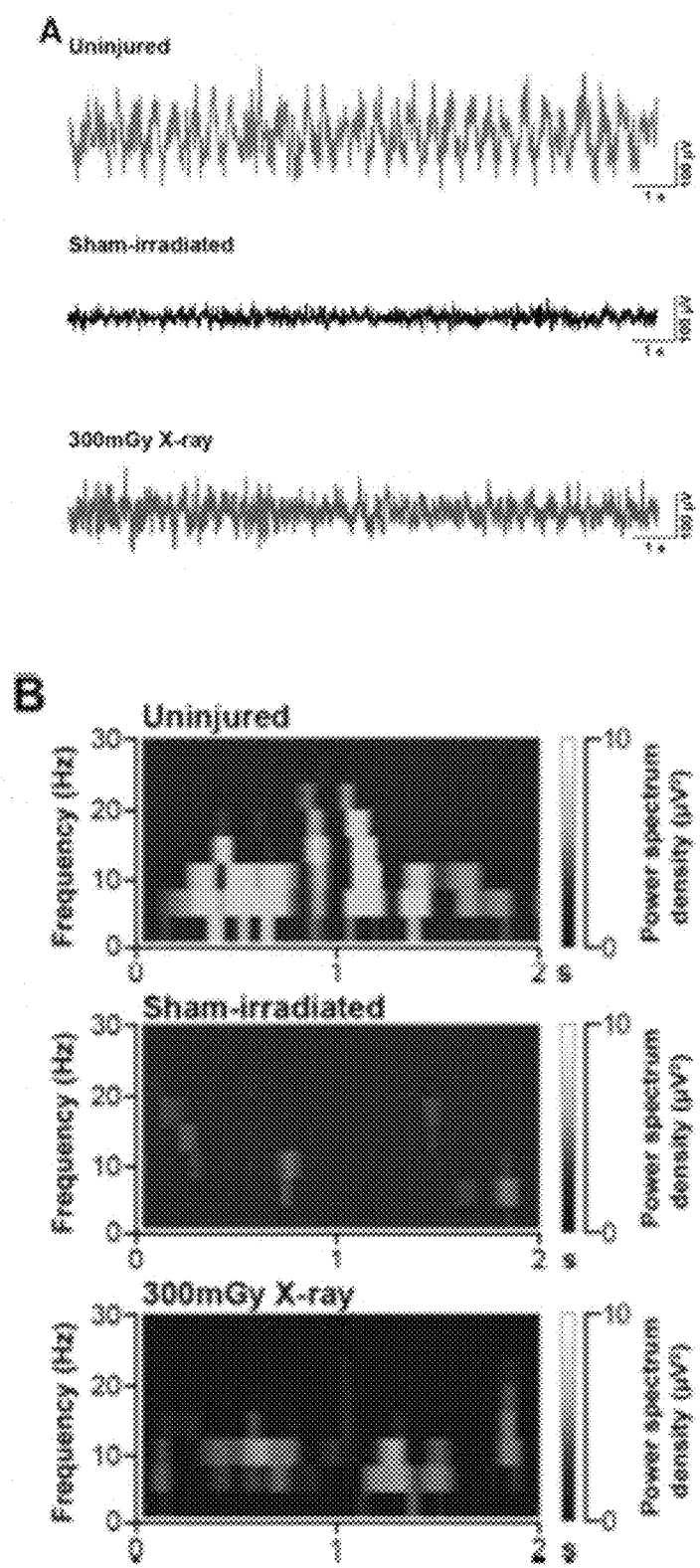
Figure 8:
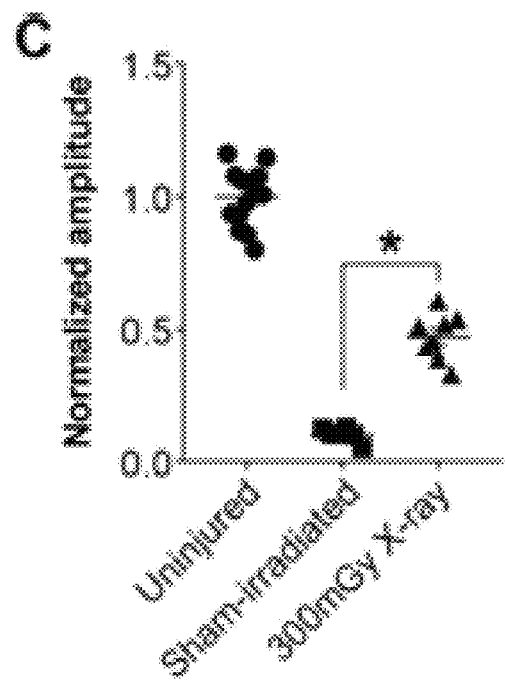

FIG. 8 depicts LD X-ray irradiation improves brain activity in the motor cortex after ischemic stroke. (A) Compared with uninjured motor cortex, EEG signals were significantly suppressed in sham-irradiated mice 8 weeks after ischemic stroke. The brain activity was markedly improved in LD X-ray irradiated mice, which correlated well with the motor functional recovery as observed in those mice. (B) Representative spectrogram indicated a marked reduction in brain activity from motor cortex in sham-irradiated mice 8 weeks after ischemic stroke, a situation which was markedly improved in LD X-ray irradiated mice. (C) The maximal peak amplitude of local field potential (LFP) was largely reduced in sham-irradiated mice. In contrast, LD X-ray irradiated mice displayed a significantly larger LFP amplitude 8 weeks after ischemic stroke. Mean±SEM (n=6-8 per group). *P<0.05; one-way ANOVA followed by Bonferroni's post hoc test.

Figure 9:
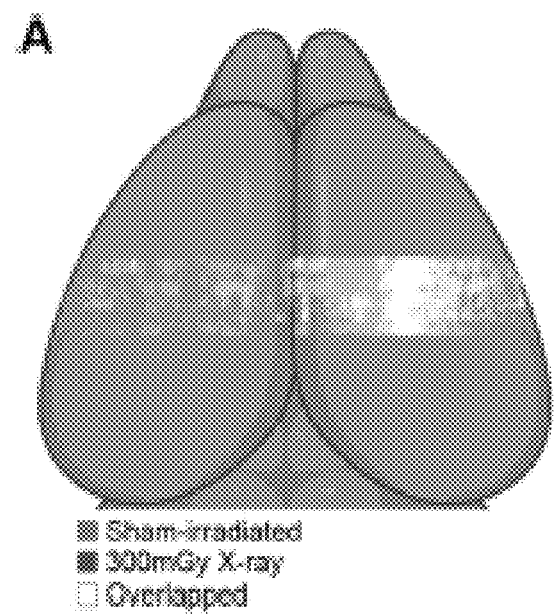
Figure 9:
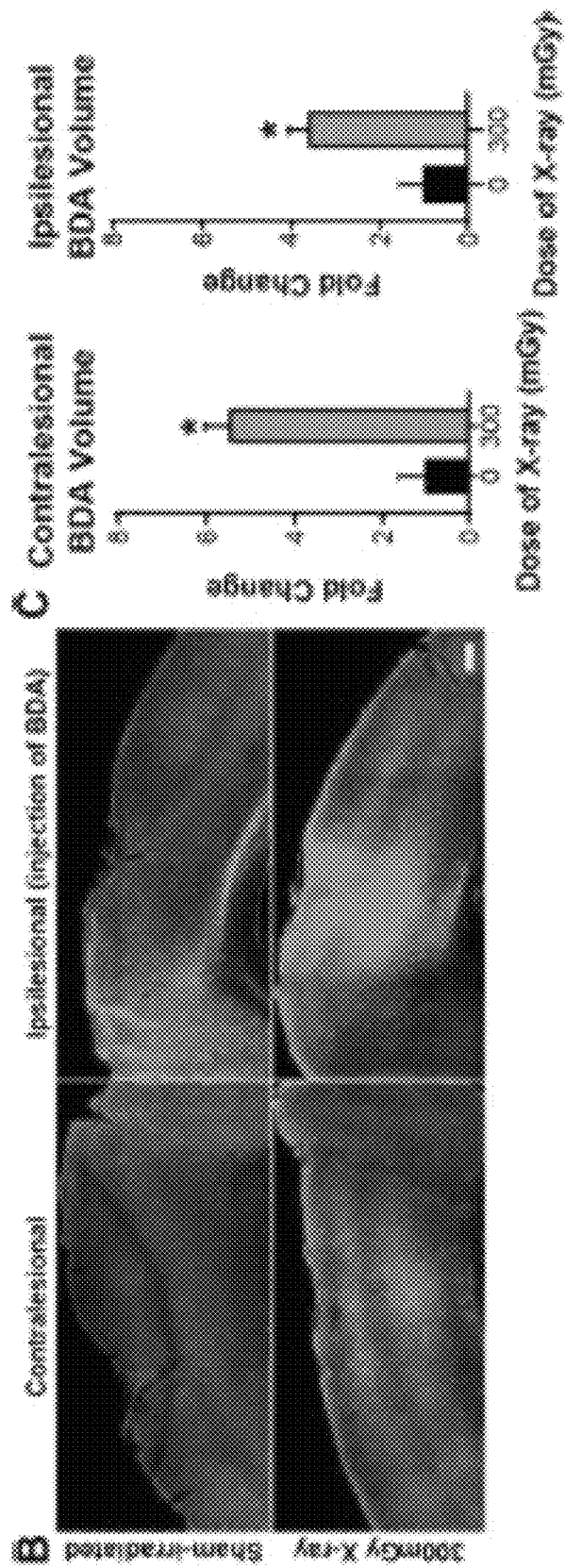
Figure 9:
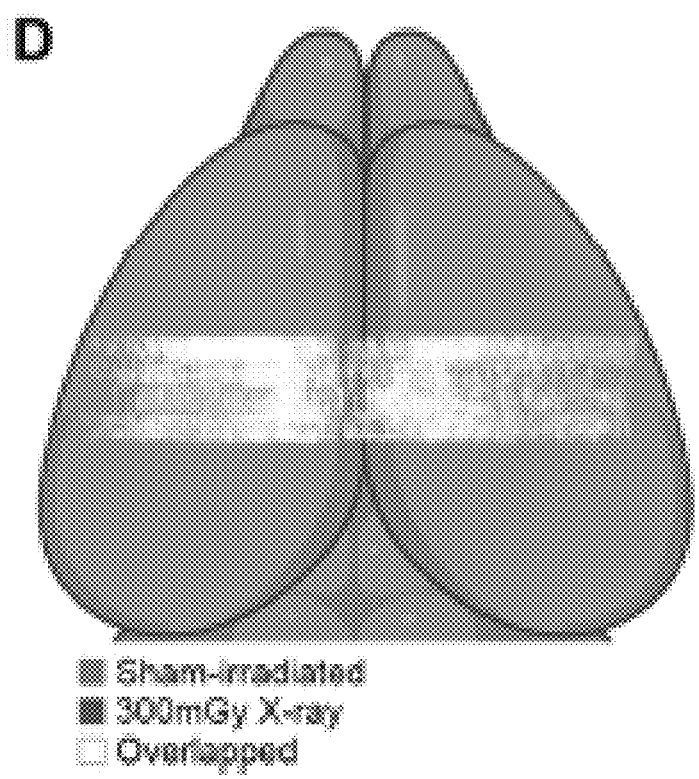
Figure 9:
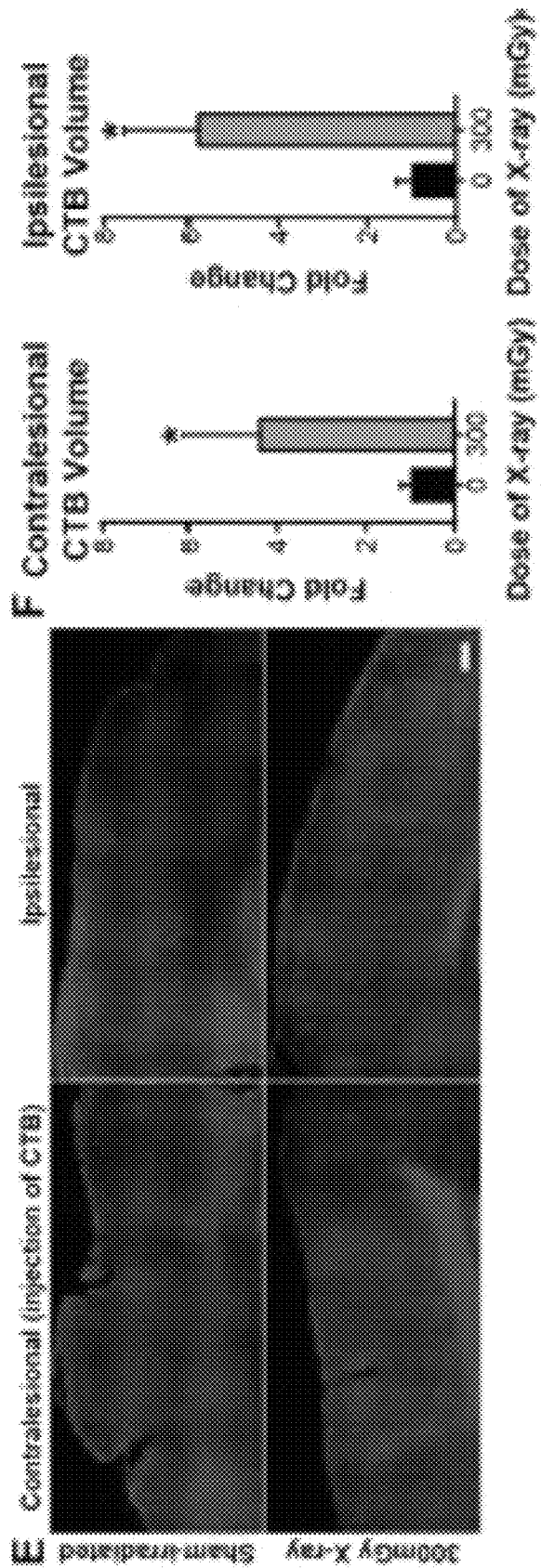

FIG. 9 depicts LD X-ray irradiation induces robust axonal sprouting after ischemic stroke. Two months after stroke, CTB-555 was microinjected into the contralesional (left) cortex. On the same mouse, BDA was microinjected into the ipsilesional (right) cortex. The brains were harvested 1 week after microinjection of both neuroanatomical tracers. (A and B) While BDA-positive axonal fibres were restricted into the ipsilesional motor cortex in sham-irradiated mice, widespread of BDA-positive axonal fibres were found in multiple areas of ipsilateral cortex, including motor and sensorimotor cortex in X-ray irradiated mice. In those mice, some of the axons could sprout into the contralesional motor cortex. (C) Quantification of BDA-positive axonal fibres revealed a marked increase in axonal density at both contralesional and ipsilesional cortex in X-ray irradiated mice, compared with sham-irradiated controls. (D and E) In X-ray irradiated mice, abundant axonal fibres were sprouted from the contralesional towards the ipsilesional cortex to facilitate brain rewiring after ischemic stroke. In sham-irradiated mice, only a few axonal fibres from contralesional cortex could sprout into ipsilesional cortex, which largely limited motor functional recovery in those mice. Scale bars: 200 μm in (B and E). (F) Quantification of CTB-positive axonal fibres suggested that LD X-ray irradiation induced robust local axonal sprouting in contralesional cortex, as well as sprouting into ipsilesional cortex. Mean of SEM (n=4-5 per group). *P<0.05, Student's ttest.

Figure 10:
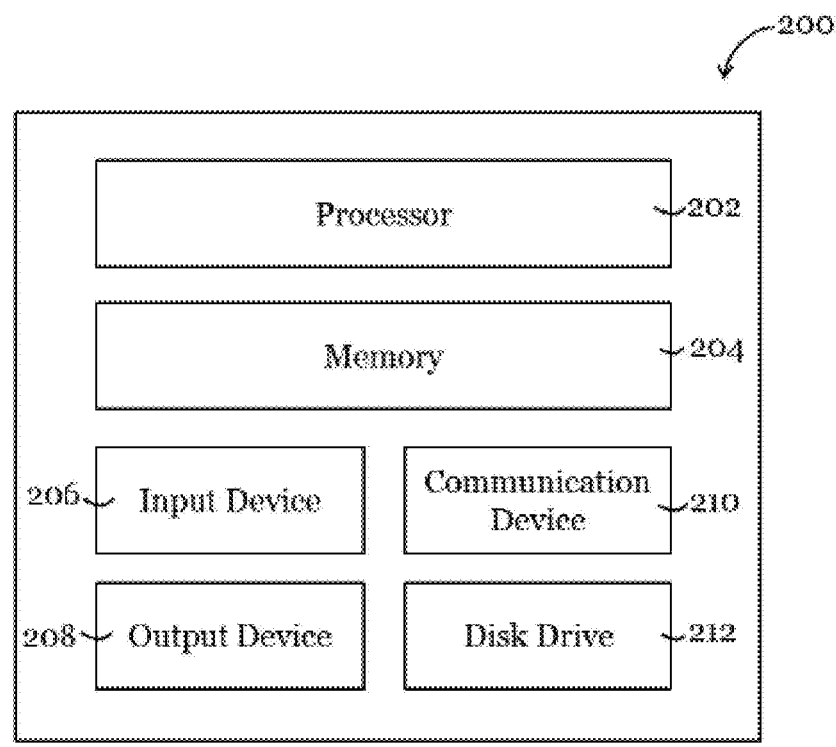

FIG. 10 depicts a schematic diagram of an exemplary information handling system in accordance with certain embodiments described herein.

DETAILED DESCRIPTION

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

An "effective amount" of radiation is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and overcome the disease itself.

The term "therapeutically effective amount" as used herein, means that amount of active compound or pharmaceutical agent that elicits a biological or medicinal in a subject that is being sought by a researcher, veterinarian, clinician, or physician, which includes alleviation of the symptoms of the disease, condition, or disorder being treated.

"Treatment," "treat," or "treating," as used herein covers any treatment of a disease or condition of a mammal, particularly a human, and includes: preventing the disease or condition from occurring in a subject which may be predisposed to the disease or condition but has not yet been diagnosed as having it; inhibiting the disease or condition, i.e., arresting its development; relieving and or ameliorating the disease or condition, i.e., causing regression of the disease or condition; or curing the disease or condition, i.e., stopping its development or progression. The population of subjects treated by the methods of the invention includes subjects suffering from the undesirable condition or disease, as well as subjects at risk for development of the condition or disease.

The term "treatment session" as used herein is a broad term and is not limited to the following, but generally includes at least one implementation of radiation therapy that treats the target area, e.g., brain or whole-body of the subject. For example, in certain embodiments, a treatment session can include one irradiation of radiation to the subject. In some embodiments, a treatment session may include more than one irradiations of radiation to the subject. In certain embodiments, the treatment session is limited, for example, when the subject visits the clinic or hospital only once for treatment, but in certain embodiments, the subject visits the clinic or hospital multiple times. In some cases, treatment sessions can be divided into multiple sessions. In certain embodiments, a treatment session can include a single treatment that provides radiation therapy, and in some embodiments, a treatment session can include multiple treatments that follow different protocols for each treatment.

The term "subject" as used herein refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In certain embodiments, the subject is a human. The subject may be undergoing other forms of treatment.

The term "co-administration" or the like, as used herein, is meant to encompass administration of radiation and the selected therapeutic agent(s) to a single subject, and is intended to include treatment regimens in which the radiation and the agent(s) are administered at the same or different time.

The term "brain injury" refers to any and all injury of the brain and can be caused by fracture or penetration of the skull (i.e. a vehicle accident, fall, gunshot wound), a disease process (i.e. neurotoxins, infections, tumors, metabolic abnormalities, etc.) or a closed head injury such as in the case of rapid acceleration or deceleration of the head (i.e. Shaken Baby Syndrome, blast), blunt trauma, concussions, and concussion syndrome.

The terms "traumatic brain injury" or "TBI" as used interchangeably herein can refer to a complex injury or injuries with a broad spectrum of symptoms and disabilities. TBI can be an acute event similar to other injuries. TBI can be classified as "mild," "moderate," or "severe." The causes of TBI are diverse and can include, for example, physical shaking by a person, a car accident, injuries from firearms, cerebral vascular accidents (e.g., a stroke), falls, explosions or blasts and other types of blunt force trauma. Other causes of TBI include the ingestion and/or exposure to one or more chemicals or toxins (such as molds, asbestos, pesticides and insecticides, organic solvents, paints, glues, gases (such as carbon monoxide, hydrogen sulfide, and cyanide), organic metals (such as methyl mercury, tetraethyl lead and organic tin), drugs (such illicit drugs), or combinations thereof). Alternatively, TBI can occur in subjects suffering from an autoimmune disease, a metabolic disorder, a brain tumor, hypoxia, a virus, meningitis, hydrocephalus or combinations thereof. Young adults and the elderly are the age groups at highest risk for TBI. In certain embodiments herein, traumatic brain injury or TBI comprises stroke and ischemia.

The term "mild TBI" and "mild traumatic brain injury" as used interchangeably herein refer to a brain injury where loss of consciousness is brief and usually a few seconds or minutes and/or confusion and disorientation is shorter than 1 hour. Mild TBI can also be referred to as a concussion, minor head trauma, minor TBI, minor brain injury, and minor head injury. While MRI and CT scans are often normal, the individual with mild TBI may have cognitive problems, such as headache, difficulty thinking, memory problems, attention deficits, mood swings, and frustration. Mild TBI is the most prevalent TBI and is often missed at time of initial injury. Mild TBI can have a Glasgow Coma scale number of between 13-15. Fifteen percent (15%) of people with mild TBI have symptoms that last 3 months or more. Mild TBI is defined as the result of the forceful motion of the head or impact causing a brief change in mental status (confusion, disorientation or loss of memory) or loss of consciousness for less than 30 minutes. Common symptoms of mild TBI include fatigue, headaches, visual disturbances, memory loss, poor attention/concentration, sleep disturbances, dizziness/loss of balance, irritability-emotional disturbances, feelings of depression, and seizures. Other symptoms associated with mild TBI include nausea, loss of smell, sensitivity to light and sounds, mood changes, getting lost or confused, and/or slowness in thinking.

The terms "Moderate TBI" and "moderate traumatic brain injury" as used interchangeably herein refers to a brain injury where loss of consciousness and/or confusion and disorientation can be between 1 and 24 hours and the subject can have a Glasgow Coma scale number of between 9-13. The subject with moderate TBI can have abnormal brain imaging results.

The terms "Severe TBI" and "severe traumatic brain injury" as used interchangeably herein refers to a brain injury where loss of consciousness can be more than 24 hours and memory loss after the injury or penetrating skull injury can be longer than 24 hours and the subject can have a Glasgow Coma scale number between 3-8. The deficits range from impairment of higher level cognitive functions to comatose states. Survivors may have limited function of arms or legs, abnormal speech or language, loss of thinking ability or emotional problems. Individuals with severe injuries can be left in long-term unresponsive states. For many people with severe TBI, long-term rehabilitation is often necessary to maximize function and independence.

The present disclosure provides a method of treating a traumatic brain injury in a subject in need thereof, the method comprising administering to the subject a therapeutically effective amount of radiation.

The radiation can be X-ray radiation, gamma ray radiation, and a combination thereof. In certain embodiments, the radiation is X-ray radiation.

Other forms of radiation useful in the methods described herein include, but are not limited to, visible light, lasers, infrared, microwave, radio frequencies, ultrasound, ultraviolet radiation, and other electromagnetic radiation. Other forms of energy can be employed in place of radiation in the methods described herein including, but not limited to, electrons, protons, ion beams such as beams of carbon ions, and neutrons.

The total amount of radiation administered in one or more treatment sessions can be in the range of about 1 mGy to about 30,000 mGy, about 1 mGy to about 25,000 mGy, about 1 mGy to about 20,000 mGy, about 100 mGy to about 20,000 mGy, about 500 mGy to about 20,000 mGy, about 1,000 mGy to about 20,000 mGy, about 1,000 mGy to about 15,000 mGy, about 1,000 mGy to about 10,000 mGy, about 5,000 mGy to about 15,000 mGy, about 7,000 mGy to about 12,000 mGy, about 5,000 mGy to about 10,000 mGy, about 1,000 mGy to about 9,000 mGy, about 1,000 mGy to about 8,000 mGy, about 1,000 mGy to about 7,000 mGy, about 1,000 mGy to about 6,000 mGy, about 1,000 mGy to about 5,000 mGy, about 1,000 mGy to about 4,000 mGy, about 1,000 mGy to about 3,000 mGy, about 1,000 mGy to about 2,000 mGy, 1 mGy to about 2,000 mGy, about 1 mGy to about 1,500 mGy, about 1 mGy to about 1,000 mGy, about 10 mGy to about 1,000 mGy, about 100 mGy to about 1,000 mGy, about 100 mGy to about 900 mGy, about 100 mGy to about 800 mGy, about 100 mGy to about 700 mGy, about 200 mGy to about 700 mGy, about 200 mGy to about 600 mGy, about 200 mGy to about 500 mGy, about 300 mGy to about 500 mGy, about 350 mGy to about 450 mGy, or about 300 mGy.

The radiation can be administered to the subject at a rate of about 500 mGy/min or less, about 400 mGy/min or less, about 300 mGy/min or less, about 200 mGy/min or less, about 150 mGy/min or less, about 100 mGy/min or less, or about 50 mGy/min or less for the amount of time required to administer the total amount of radiation for the given treatment session. In certain embodiments, radiation is be administered to the subject at a rate of about 50 mGy/min to about 500 mGy/min, 50 mGy/min to about 400 mGy/min, 50 mGy/min to about 300 mGy/min, 50 mGy/min to about 250 mGy/min, 50 mGy/min to about 200 mGy/min, 50 mGy/min to about 150 mGy/min, 50 mGy/min to about 100 mGy/min, 70 mGy/min to about 90 mGy/min, or about 80 mGy/min for the amount of time required to administer the total amount of radiation for the given treatment session.

In certain embodiments, the treatment session may be limited to about 1 day, and in certain embodiments, the treatment session is about 2 days, about 3 days, about 5 days, about 1 week, about 10 days. It may be days, about 2 weeks, about 3 weeks, about 1 month, about 6 weeks, about 2 months, about 3 months, about 6 months, about 1 year, or more. In certain embodiments, the treatment session is limited to the administration of radiation in a single dose.

The radiation described herein can be administered according to therapeutic protocols well known in the art. Also, in accordance with the knowledge of the skilled clinician, the therapeutic protocols (e.g., dosage amounts, dosage rates, and times of administration) can be varied in view of the observed effects of the radiation on the subject.

The TBI can be a mild TBI, a moderate TBI, a moderate-severe TBI, or a severe TBI. The TBI can be the result of an injury sustained by physical shaking by a person (such as an infant), a car accident, a firearm, a stroke, falls, explosions, blasts and other types of blunt force trauma, ingestion and/or exposure to one or more chemicals or toxins (such as molds, asbestos, pesticides and insecticides, organic solvents, paints, glues, gases (such as carbon monoxide, hydrogen sulfide, and cyanide), organic metals (such as methyl mercury, tetraethyl lead and organic tin), drugs (such illicit drugs), or combinations thereof), an autoimmune disease, a metabolic disorder, a brain tumor, hypoxia, a virus, meningitis, hydrocephalus or combinations thereof.

In certain embodiments, the TBI comprises a stroke. The stroke can be any one of the 30 different forms stroke, including an ischemic stroke, a hemorrhagic stroke, a transient ischemic attack, or a brain stem stroke. Stroke as used herein, is used in the broadest sense, and includes all forms of stroke, whether specifically listed herein or not. In certain embodiments, the TBI comprises an ischemic stroke.

In certain embodiments, the method described herein further comprises the step of co-administering a therapeutically effective amount of a traumatic brain injury therapeutic.

Examples of traumatic brain injury therapeutics include, but are not limited to, aspirin, intercellular adhesion molecule (ICAM)-1 and LFA-1 antagonists 20 including antibodies, human anti-leukocytic antibodies, such as Hu23F2G, glycoprotein IIb/IIIa antagonists such as eptifibatide, direct thrombin inhibitors, external or local ultrasound, mechanical clot retrieval or inaceration, fibrinolytic agents, neuronal wound healing agents, such as basic fibroblast growth factor, neuroprotective agents, such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation, antioxidants, anti-adhesion monoclonal antibodies and antagonists and antibodies inhibiting platelet aggregation, such as argatroban and abciximab, phenytoin, nitrogen oxides, CNS-protective therapies, free-radical scavengers such as tirilazad, reactive oxygen metabolites, and antioxidants, and other thrombolytic agents, such as, acylated plasminogen-streptokinase activator complex, single-chain urokinase-plasminogen activator, thrombin-like enzymes from snake venoms, such as ancrod, streptokinase, urokinase, anistreplase, alteplase, saruplase, reteplase, lanoteplase, plasmin, a truncated form of plasmin, recombinant desmodus rotundus salivary plasminogen activator alpha-1, a mutant fibrin-activated human plasminogen, staphylokinase, fibrolase, prourokinase, monteplase, pamiteplase, tisokinase, and vampire bat plasminogen activator, an astrocyte-function-improving agent such as that disclosed in US 2004/0176347, a spin-trap agent such as NXY-059, clopidogrel, n-methyl-dextro-aspartic acid receptor blocking agent, an anticonvulsive agent, a caspase 3 inhibitor, ((tert-butylimino)methyl) 1,3-(benzenedisulfonate disodium n-oxide), ebselen, glutathione peroxidase, norphenazone, rovelizumab, lactacystin beta-lactone, tsukubaenolide, phosphonomethylpipecolic acid, eliprodil, antibodies to ganglioside GM1, and biologically active variants, salts, prodrugs, and analogs thereof.

The traumatic brain injury therapeutics described herein can be administered according to therapeutic protocols well known in the art. It will be apparent to those skilled in the art that the administration of the radiation described herein and the traumatic brain injury therapeutics can be varied depending on the TBI being treated and the known effects of traumatic brain injury therapeutic on that TBI. Also, in accordance with the knowledge of the skilled clinician, the therapeutic protocols (e.g., dosage amounts and times of administration) can be varied in view of the observed effects of the administered traumatic brain injury therapeutic on the subject, and in view of the observed responses of the TBI to the administered traumatic brain injury therapeutic.

The particular choice of traumatic brain injury therapeutic will depend upon the diagnosis of the attending physicians and their judgment of the condition of the subject and the appropriate treatment protocol.

The radiation and the traumatic brain injury therapeutic may be administered concurrently (e.g., simultaneously, essentially simultaneously or within the same treatment protocol) or sequentially, depending upon the nature of the TBI, the condition of the subject, and the actual choice of the traumatic brain injury therapeutic to be administered in conjunction (i.e., within a single treatment protocol) with the radiation.

This disclosure, in one aspect, reports the discovery of the therapeutic potential of whole-body LD X-ray irradiation for TBI. Previous reports had demonstrated that low dose ionizing radiation induces production of anti-inflammatory cytokines and stimulates chemotactic response in immune cells. Thus, the neuroprotective effects of LD X-ray irradiation after a cortical stab wound TBI were evaluated. In an experiment, the mice received a single acute exposure of whole-body X-ray irradiation at 300 mGy immediately after TBI. The observation was: a substantial increase in microglial density and reduction of growth inhibitory chondroitin sulfate proteoglycan (CSPG) deposition at the lesion site of X-ray irradiated mice 6 hours (FIG. 1) and 7 days (FIG. 2) after TBI. The size of wound area was markedly reduced in X-ray irradiated mice compared with sham-irradiated controls (FIG. 3), which indicates the beneficial effect of whole-body LD X-ray irradiation on TBI. More importantly, a single acute exposure to whole-body LD X-ray irradiation markedly accelerated motor functional recovery after TBI as demonstrated by a battery of animal neurobehavioral tests. Sham-irradiated mice showed severe motor deficit in beam walking test during the first week after TBI, and gradually returned to baseline values by 28 days post injury. X-ray irradiated mice took only 7 days to recover to baseline values (FIGS. 4A and 4B) and showed significantly fewer foot slips than the sham-irradiated controls (FIG. 4C). In pole climbing test, sham-irradiated mice spent more time to descend from the pole at the beginning and only managed to descend properly at day 28 post injury. In contrast, X-ray irradiated mice showed mild motor deficit during the first week of TBI, and returned to baseline values as earlier as day 7 post injury (FIGS. 4D and 4E). The grip strength of forelimbs (FIG. 4F) and hindlimbs (FIG. 4G) of X-ray irradiated mice were significantly higher than sham-irradiated mice at all time points tested during the first three weeks after TBI.

This disclosure, in another aspect, reports the discovery of the therapeutic potential of whole-body LD X-ray irradiation for ischemic stroke. In an experiment, ischemic stroke was induced in primary motor (M1 and M2) and somatosensory (S1) area by a photosensitive dye Rose Bengal in mice. The mice received a single acute exposure of whole-body X-ray irradiation at 300 mGy immediately after stroke induction. On post-stroke day 1 and 3, the observation was: a marked reduction in infract volume in X-ray irradiated mice compared with sham-irradiated controls (FIG. 5). The wound area was markedly reduced in X-ray irradiated mice at day 7 after stroke induction, demonstrating an accelerated wound closure after X-ray irradiation (FIG. 6). The behavioral test data also suggested a strong beneficial effect of X-ray irradiation on motor functional recovery after ischemic stroke. In beam walking test, sham-irradiated mice showed sustained and irreversible motor deficits during the entire testing period of 8 weeks, a situation that completely reversed after an acute exposure to LD X-ray irradiation. On the other hand, the irradiated mice showed mild motor deficits and were able to transverse the narrow beam even on the next day after stroke induction, and were fully recovered within 7 days post stroke (FIGS. 7A and 7B). X-ray irradiated mice demonstrated a marked improvement in motor function while performing pole climbing (FIGS. 7C and 7D). The grip strength of forelimbs (FIG. 7E) and hindlimbs (FIG. 7F) in X-ray irradiated mice were significantly higher than the sham-irradiated controls. Electroencephalography (EEG) recordings on sham-irradiated mice revealed a significant reduction in EEG frequency power spectrum after stroke (FIGS. 8A and 8B). The maximum amplitude of local focal potential (LFP) in the injured motor cortex was reduced significantly when compared with the uninjured (contralateral) motor cortex (FIG. 8C), which correlated well with sustained and irreversible motor function deficit observed in sham-irradiated stroke mice. Strikingly, LD X-ray irradiation induced recovered at least half of the EEG activities and LFP amplitudes (FIGS. 8B and 8C).

Injection of biotinylated dextran amines (BDA) at the injury site revealed that increased axonal sprouting was observed in LD X-ray irradiated mice at the ipsilesional cortex (FIGS. 9A and 9B). Some of the sprouted axons could regenerate across the lesion to reach the contralesional cortex after X-ray irradiation (FIG. 9C). Cholera toxin subunit B (CTB) was injected into the contralesional cortex in the same animal to examine if uninjured axonal fibers sprout into the injured side of the brain. X-ray irradiation induced robust axonal sprouted from the contralesional cortex to the injured side of the brain (FIGS. 9D and 9E). The observation was a marked increase in CTB-positive axonal fibers in the ipsilesional cortex, which were originated from uninjured contralesional cortex (FIG. 9F), and which suggests a significant brain rewiring in X-ray irradiated mice after ischemic stroke. Collectively, the experimental data suggested that an immediate acute exposure to LD X-ray irradiation of 300 mGy was sufficient in some cases to completely reverse motor deficits by preserving the brain activity and rewiring of motor cortex for functional recovery after stroke.

The disclosure is further illustrated by the following examples, which are not to be construed as limiting this disclosure in scope or spirit to the specific procedures herein described.

EXAMPLES

Animal Model of Traumatic Brain Injury

In one example, a cortical stab wound injury model was used as an animal model of TBI, which possess significant motor deficits after injury with typical hallmark neuro-inflammation features of TBI, including activation and migration of microglia towards the lesion and increased chondroitin sulfate proteoglycan (CSPG) deposition at the lesion core after injury. All animal experiments were conducted in accordance with approved ethical protocols. Mice were provided with sufficient food and water ad libitum, and were maintained with a 12:12 h light-dark cycle. Cortical stab wound injuries were performed on adult C57BL/6 mice for the assessment of microglial density and CSPG deposition 1 and 7 days after injury. The mice were first anesthetized using ketamine (100 mg/kg) and xylazine (10 mg/kg) and placed in the stereotactic apparatus (Stoelting). A midline incision was made through the scalp, and skin was retracted laterally. A scalpel blade (#10) was inserted at 2 mm posterior to bregma and 1 mm lateral to the bregma with its depth of 5 mm from the skull, and the scalpel blade was left in place for 3 minutes to ensure complete incision, and finally skin incision was closed with 5-0 suture (Ethilons). Injured postnatal and adult mice were placed on heat pad for 1 hour post-surgery, and then returned to their cages immediately after sham- or X-ray irradiation.

Animal Model of Ischemic Stroke

Photothrombotic stroke model was used as an animal model of ischemic stroke. The adult male C57BL/6 mice were first anesthetized with ketamine (100 mg/kg) and xylazine (10 mg/kg), and placed in the stereotactic apparatus (Stoelting). Rose Bengal was first dissolved in saline at a final concentration of 10 mg/ml, and 150 µl of Rose Bengal (10 mg/ml) was injected intraperitoneally into each mouse. A midline incision was made through the scalp, and skin was retracted laterally. Five minutes after injection of Rose Bengal, a cold light source (Leica CLS150XE) was positioned 1.5 mm lateral from the bregma which included a large portion of primary motor cortex. The brains were illuminated through the intact skull for 10 minutes with maximum light intensity of 150 W. This generated a focal photothrombotic stroke at the illuminated area in 4-6 hours. After illumination, the skin was sutured using 5-0 suture (Ethilons). The injured mice were allowed to recovery on a heat pad for 1 hour and returned to their home cages immediately after sham- or X-ray irradiation.

Methodology for Whole-Body LD X-Ray Irradiation

Immediately after cortical stab wound injury or induction of ischemic stroke, animals were subjected to a single exposure of whole-body X-ray irradiation at 300 mGy using a cabinet Xray irradiator X-Rad 320 (Precision X-Ray) equipped with a beam-conditioning filter (1.5 mm Aluminum, 0.25 mm Copper and 0.75 mm Tin) at a focus-to-surface distance (FSD) of 70 cm. To ensure that each animal received the same and even amount of radiation inside the pie cage in different, X-ray irradiator was calibrated before every experiment using a dosimeter (UNIDOS® E Dosemeter, Precision X-Ray). Dosimeter was placed inside the pie cage where the animals were held during X-ray irradiation to measure the actual dosimetry that the animals were exposed and should match with the input dose values. During irradiation, pie cage was placed on a slowly rotating turntable at 4 rpm to allow uniform X-ray irradiation. The voltage and current of the X-ray irradiator were set at 320 kV and 2 mA, respectively, to achieve a dose rate of 80 mGy/min. The mice were subjected to a single dose of X-ray irradiation at 300 mGy. Sham irradiation was performed by placing the mice into the cabinet for the equivalent timer period of X-ray irradiation at 300 mGy) without switching on the X-ray irradiator.

Quantification of Microglial Density and Chondroitin Sulfate Proteoglycan (CSPG) Fluorescence Intensity at the Lesion The microglial density and CSPG deposition were examined at the acute (6 hours in TBI model and 1 day in stroke model) and chronic (7 days for both models) phases after injury. The postnatal or adult mice were perfused transcardially with 4% paraformaldehyde (PFA), and whole brains were harvested, post-fixed, cryoprotected and frozen in OCT compound (Tissue-Tek) at 6 hours or 7 days after cortical stab wound injuries. 16 μm thick sagittal sections of brains were blocked with 0.5% bovine serum albumin (BSA)/0.5% Triton X-100 (Sigma Aldrich) in PBS, and incubated with primary antibodies against anti-NF200 (1:1,500; Millipore), anti-IBA-1 (1:500; Wako), and anti-CS56 (1:200; Sigma Aldrich) for overnight at 4° C. After three times of washing with PBS, cryosections were incubated with corresponding secondary antibodies conjugated with Alexa Fluor 488, Alexa Fluor 555, and Alexa Fluor 647 (1:300, Molecular Probes), respectively. Images were acquired at 20× magnifications using Nikon Ni-E epifluorescence microscope equipped with motorized stage.

Quantification of Wound Closure After Traumatic Brain Injury and Ischemic Stroke Seven days after cortical stab wound injury or induction of ischemic stroke, PFA-fixed brains were harvested, and 20 μm thick sagittal sections were prepared. Sagittal sections of brain were stained with cresyl violet and imaged at 10× magnifications using Nikon Ni-E microscope equipped with a digital camera. One in every fifth 20 μm thick PFA-fixed brain sagittal cryosections per mouse (100 μm apart) were stained with cresyl violet for wound size measurement, to ensure covering the entire injury site. Boundary of injury site was outlined as demonstrated by reduced creysl violet staining intensity and the area of wound size was determined using NIS-Elements software and presented as mm2. For quantification, contour of injury site was outlined manually as regions of interest (ROIs) using NIS-Elements software (Nikon). Total number of IBA-1-positive microglia within each ROI was manually counted using NIS-Elements software, and the area (in mm2) of injury site of each section was measured. The microglial cell density was calculated as total number of IBA-1-positive microglia per mm2, and presented as fold change. The immunoreactivity of CSPG was quantified as integrated raw fluorescent intensity using NIS-Elements software and normalized with the area of ROI at the injury site. For each animal, the average microglial cell density, and CSPG immunoreactivity were quantified from at least 5 sections (48 μm apart). At least 3 animals from each treatment group were used to determine the average microglial cell density and CSPG immunoreactivity.

Animal Behavioral Assessment for Motor Functional Recovery After Traumatic Brain Injury and Ischemic Stroke A week before TBI or ischemic stroke, adult male C57BL/6 mice were habituated and trained for three sessions (30 minutes per session). Baseline values of each behavioral assessment were taken a day before the injury. Motor functional recovery were monitored at day 1, 3, 5, 7, 14, 21, 28 (for TBI), 35 and 42 days (for ischemic stroke) post injury with 30 minutes apart from each test. The observer of the animal behavioral assessment was blinded to treatments. Beam walking test: Fine motor coordination and body balance were evaluated using beam walking test after cortical stab wound injury. Mice were trained to walk across a wooden round beam with 100 cm long, 1 cm diameter, and 50 cm above the bench, and behavior was recorded by an overhead video camera over a period of 2 minutes using ANYmaze automated video tracking system (Stoelting, USA). In case of a fall during training, mice were placed back immediately to the starting and allowed to walk across the beam again. Baseline values were taken after they completed the training sessions successfully. The mice were then tested for three times in three separated sessions with at least 20 minutes interval. In case of a fall during the tests, the maximum time of 120 second was recorded. The motor activity of animals in each treatment group was depicted by the heatmap plot generated by the ANY-maze video tracking software. Latency to transverse the beam was determined. The number of foot slip errors were recorded manually (determined by a paw slipping off the beam) by viewing the video clips. Pole climbing test: Mice were placed head-up on top of a wooden pole with a rough surface (50 cm in height, 1 cm in diameter), turning around on the rod, releasing grip from the forelimbs, rotation of the trunk and supporting of the body by the hindlimbs during this maneuver, descend with the head facing downwards, and the latency to reach the platform were record using ANY-maze software (Stoelting, USA). During the training session, mice were allowed to descend the pole repeatedly (even after fall) within 2 minutes. During the actual experiment sections, the mice were given a maximum time of 2 minutes to complete the task. In case of a fall from the pole, maximum time (i.e. 120 s) was recorded for that trial. The motor activity of animals in each treatment group was depicted by the heat-map plot generated by the ANY-maze video tracking software. Grip strength test: The grip strength of forelimbs or hindlimbs were measured using grip strength meter (GT-3, Bioseb). To measure the grip strength of forelimbs, mouse forelimbs were placed on the T-bar of the grip strength meter, and gently pull off until the grip was released from the bar. To assess the grip strength of hindlimbs, forelimbs were rested on a plastic bar, hindpaws were positioned to grip T-bar and pulled off. Values at which the mouse forelimbs or hindlimbs left the T-bar were designated as grip strength in grams recorded by gripmeter. The mice were tested for five times in two separated sessions with at least 30 minutes interval. The final value of grip strength represented the average value obtained from 5 trials.

TTC Staining

A well-established 2,3,5-triphenyltetrazolium chloride (TTC) staining protocol was used to measure the brain infract volume after ischemic stroke. Briefly, the brains were freshly dissected and immediately snap frozen on ice for 5 minutes, placed onto an ice-cold brain matrix (RWD Life Science) and cut into a series of 2-mm-thick brain slices. The brain slices were then transferred to 2% TTC solution (Sigma) in PBS and incubated at 37° C. for 20 minutes. The stained slices were post-fixed with 4% PFA and imaged using Nikon SMZ1270 Stereomicroscope equipped with a digital camera. Healthy brain tissues were stained in red while the dead tissue remained unstained by TTC solution. Infract volume was determined manually using NIS-Elements software and presented as $mm^3$.

Electroencephalography (EEG) Recordings on Motor Cortex

Eight weeks after stroke induction, the mice were anaesthetized with ketamine (100 mg/kg) and xylazine (10 mg/kg) and placed onto a stereotactic frame. Mice were implanted bilaterally with epidural recording electrodes made of stainless-steel over parietal (motor) cortex (2 mm A/P, 2 mm M/L with reference to bregma). Reference electrode was implanted over frontal bone, and fixed to the skull with dental cement. Buprenorphine (75 μg/kg) was administered before and after implantation to relief pain relief, and the mice were allowed to recover for 3 to 5 days before EEG recordings. The EEG signals were recorded on a freely moving mouse for 30 minutes using a data acquisition system (Medusa System, Bio-Signals Technologies). Derivation of raw signal processing and analysis of spectrogram were analyzed by Spike2 software (Cambridge Electronic Design). The maximum peak amplitude of local field potential (LFP) was obtained by averaging the amplitude envelope time series (i.e. 30 minutes) using Hilbert transformation of filtered LFPs using a customized MATLAB program.

Anterograde Axonal Tracing Using Biotinylated Dextran Amines (BDA) and Cholera Toxin Subunit B (CTB)

Eight weeks after stroke induction, 0.6 µl of 10% biotinylated dextran amines (BDA) solution was injected to the pre-motor cortex (1.8 mm A/P, 1.75 mm M/L, 0.75 mm D/V with reference to bregma) of the right (injured) hemisphere 34. On the same mice, 0.6 µl of cholera toxin subunit B conjugated with Alexa Fluor 555 (CTB-555; 2 µg/µl) was injected to the pre-motor cortex of the left (uninjured) hemisphere. The mice were perfused with 4% PFA, and the whole brains were harvested, post-fixed and cryoprotected in OCT compound for cryosectioning 1 week after injections of anatomical tracers. To visualize the BDA-labeled axons, 30 µm thick coronal sections of brains were blocked with 0.5% BSA/0.5% Triton X-100 (Sigma) for 1 hour, and incubated with streptavidin conjugated with Alexa Fluor 488 for 2 hours at room temperature. BDA- or CTB-positive axonal fibres were identified automatically using NIS-Elements software with Pixel Classifier plugin. The area fractions of BDA- or CTB-positive axonal fibres within the contralesional (BDA-positive) or ipsilesional (CTB-positive) cortex were calculated using NIS-Elements software, and normalized with sham-irradiated controls.

Exemplary System

Referring to FIG. 10, there is shown a schematic diagram of an exemplary information handling system 200 that can be used as an information processing systems in one embodiment of the invention. The system 200 may be operably connected with the radiation/radioactive source/device to determine whether an animal has a medical condition (e.g., by image processing or signal analysis) and/or to control activation of the radiation/radioactive source/device. The system 200 may have different configurations, and it generally comprises suitable components necessary to receive, store, and execute appropriate computer instructions, commands, or codes. The main component of the system 200 is a processor 202 and preferably a memory 204. The processor 202 may be formed by one or more processors in the form of: central processing unit (CPU), microcontroller unit (MCU), controllers, logic circuits, Raspberry Pi chip, digital signal processor (DSP), application-specific integrated circuit (ASIC), Field-Programmable Gate Array (FPGA), or any other digital or analog circuitry configured to interpret and/or to execute program instructions and/or to process data. The memory unit 204 may include one or more volatile memory unit (such as RAM, DRAM, SRAM), one or more non-volatile memory unit (such as ROM, PROM, EPROM, EEPROM, FRAM, MRAM, FLASH, SSD, NAND, and NVDIMM), or any of their combinations. Preferably, the system 200 further includes one or more input devices 206 such as a keyboard, a mouse, a stylus, an image scanner, a microphone, a tactile input device (e.g., touch sensitive screen), and an image/video input device (e.g., camera). The system 200 may further include one or more output devices 208 such as one or more displays (e.g., monitor), speakers, disk drives, headphones, earphones, printers, 3D printers, etc. The display may include a LCD display, a LED/OLED display, or any other suitable display that may or may not be touch sensitive. The system 200 may further include one or more disk drives 212 which may encompass solid state drives, hard disk drives, optical drives, flash drives, and/or magnetic tape drives. A suitable operating system may be installed in the system 200, e.g., on the disk drive 212 or in the memory unit 204. The memory unit 204 and the disk drive 212 may be operated by the processor 202. The system 200 also preferably includes a communication device 210 for establishing one or more communication links (not shown) with one or more other computing devices such as servers, personal computers, terminals, tablets, phones, or other wireless or handheld computing devices. The communication device 210 may be a modem, a Network Interface Card (NIC), an integrated network interface, a radio frequency transceiver, an optical port, an infrared port, a USB connection, or other wired or wireless communication interfaces. The communication links may be wired or wireless for communicating commands, instructions, information and/or data. Preferably, the processor 202, the memory unit 204, and optionally the input devices 206, the output devices 208, the communication device 210 and the disk drives 212 are connected with each other through a bus, a Peripheral Component Interconnect (PCI) such as PCI Express, a Universal Serial Bus (USB), an optical bus, or other like bus structure. In one embodiment, some of these components may be connected through a network such as the Internet or a cloud computing network. A person skilled in the art would appreciate that the system 200 shown in FIG. 10 is merely exemplary and different information handling systems 200 with different configurations may be applicable in the invention. In one example, the system 200 may be integrated to or otherwise provided by the radiation/radioactive source/device.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein. It will also be appreciated that where the methods and systems of the invention are either wholly implemented by computing system or partly implemented by computing systems then any appropriate computing system architecture may be utilized. This will include stand-alone computers, network computers, dedicated or non-dedicated hardware devices. Where the terms "computing system" and "computing device" are used, these terms are intended to include any appropriate arrangement of computer or information processing hardware capable of implementing the function described.

What is claimed is:

1. A method of treating a traumatic brain injury in a subject in need thereof, the method comprising administering to the subject a therapeutically effective amount of radiation, wherein the radiation is selected from the group consisting of X-ray radiation, gamma ray radiation, and a combination thereof.

2. The method of claim 1, wherein 10,000 mGy or less of radiation is administered to the subject.

3. The method of claim 1, wherein about 2,000 mGy to about 6,000 mGy of radiation is administered to the subject.

4. The method of claim 1, wherein the radiation is administered to the subject at a rate of 200 mGy/min or less.

5. The method of claim 1, wherein the radiation is administered to the subject at a rate of about 50 to about 150 mGy/min.

6. The method of claim 1, wherein the radiation is administered to the brain.

7. The method of claim 1, wherein the radiation is administered to the whole-body.

8. The method of claim 1, wherein the traumatic brain injury comprises a mild traumatic brain injury, a moderate traumatic brain injury, or a severe traumatic brain injury.

9. The method of claim 1, wherein the traumatic brain injury comprises a moderate traumatic brain injury or a severe traumatic brain injury.

10. The method of claim 1, wherein the traumatic brain injury comprises a stroke.

11. The method of claim 10, wherein the stroke is an ischemic stroke, a hemorrhagic stroke, a transient ischemic attack, or a brain stem stroke.

12. The method of claim 1, wherein the traumatic brain injury comprises an ischemic stroke.

13. The method of claim 1, further comprising the step of co-administering a therapeutically of amount of a traumatic brain injury therapeutic.

14. The method of claim 13, wherein the traumatic brain injury therapeutic is selected from the group consisting of a neuroprotective agent, a thrombolytic agent, a glycoprotein Willa receptor antagonist, and an anti-CD 18 antibody.

15. The method of claim 1, wherein the method comprises administering to the brain or the whole-body of the subject about 10,000 mGy or less of X-ray radiation, gamma ray radiation, or a combination thereof.

16. The method of claim 1, wherein the method comprises administering to the brain or the whole-body of the subject about 200 mGy to about 400 mGy of X-ray radiation.

17. The method of claim 16, wherein the radiation is administered to the brain and the traumatic brain injury comprises a stroke.

18. The method of claim 1, wherein the method comprises administering to the brain of the subject about 200 mGy to about 400 mGy of X-ray radiation and the traumatic brain injury comprises an ischemic stroke.

19. The method of claim 1, wherein the method comprises administering to the brain of the subject X-ray radiation at a rate of about 75 mGy/min to about 100 mGy/min and the traumatic brain injury comprises an ischemic stroke.

* * * * *